United States Patent
Hwang et al.

(10) Patent No.: US 7,591,996 B2
(45) Date of Patent: Sep. 22, 2009

(54) ULTRASOUND TARGET VESSEL OCCLUSION USING MICROBUBBLES

(75) Inventors: Joo Ha Hwang, Bellevue, WA (US); Andrew Brayman, Edmonds, WA (US)

(73) Assignee: University of Washington, Seattle, WA (US)

( * ) Notice: Subject to any disclaimer, the term of this patent is extended or adjusted under 35 U.S.C. 154(b) by 204 days.

(21) Appl. No.: 11/206,639

(22) Filed: Aug. 17, 2005

(65) Prior Publication Data

US 2007/0041961 A1    Feb. 22, 2007

(51) Int. Cl.
*A61B 17/26* (2006.01)
*A61B 8/00* (2006.01)
*A61B 8/12* (2006.01)
*A61K 38/00* (2006.01)

(52) U.S. Cl. .......................... 424/9.1; 424/9.5; 600/371
(58) Field of Classification Search .................. None
See application file for complete search history.

(56) References Cited

U.S. PATENT DOCUMENTS

| | | | |
|---|---|---|---|
| RE33,590 E | 5/1991 | Dory | 128/660.03 |
| 5,039,774 A | 8/1991 | Shikinami et al. | 528/60 |
| 5,065,742 A | 11/1991 | Belikan et al. | 128/24 |
| 5,080,101 A | 1/1992 | Dory | 128/660.03 |
| 5,080,102 A | 1/1992 | Dory | 128/660.03 |
| 5,150,712 A | 9/1992 | Dory | 128/660.03 |
| 5,219,401 A | 6/1993 | Cathignol et al. | 128/660.03 |
| 5,311,869 A | 5/1994 | Okazaki | 128/660.03 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/660.03 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,522,878 A | 6/1996 | Montecalvo et al. | 607/152 |
| 5,526,815 A | 6/1996 | Granz et al. | 128/660.03 |
| 5,558,092 A | 9/1996 | Unger et al. | 128/660.03 |
| 5,573,497 A | 11/1996 | Chapelon | 601/2 |
| 5,666,954 A | 9/1997 | Chapelon et al. | 600/439 |
| 5,720,286 A | 2/1998 | Chapelon et al. | 600/439 |
| 5,720,287 A | 2/1998 | Chapelon et al. | 600/439 |
| 5,762,066 A | 6/1998 | Law et al. | 600/439 |
| 5,769,790 A | 6/1998 | Watkins et al. | 600/439 |
| 5,817,021 A | 10/1998 | Reichenberger | 600/439 |
| 5,823,962 A | 10/1998 | Schaetzle et al. | 600/439 |
| 5,827,204 A | 10/1998 | Grandia et al. | 601/2 |
| 5,833,647 A | 11/1998 | Edwards | 604/22 |
| 5,873,828 A | 2/1999 | Fujio et al. | 600/439 |
| 5,895,356 A | 4/1999 | Andrus et al. | 600/439 |
| 5,906,580 A | 5/1999 | Kline-Schoder et al. | 600/459 |
| 5,993,389 A | 11/1999 | Driscoll, Jr. et al. | 600/371 |
| 6,007,499 A | 12/1999 | Martin et al. | 601/3 |
| 6,039,694 A | 3/2000 | Larson et al. | 600/459 |
| 6,050,943 A | 4/2000 | Slayton et al. | 600/439 |
| 6,071,239 A | 6/2000 | Cribbs et al. | 600/439 |
| 6,179,831 B1 | 1/2001 | Bliweis | 606/21 |
| 6,221,015 B1 | 4/2001 | Yock | 600/439 |
| 6,409,720 B1 | 6/2002 | Hissong et al. | 606/27 |
| 6,425,867 B1 | 7/2002 | Vaezy et al. | 600/439 |
| 6,491,672 B2 | 12/2002 | Slepian et al. | 604/267 |
| 6,595,934 B1 | 7/2003 | Hissong et al. | 601/3 |
| 6,599,256 B1 | 7/2003 | Acker et al. | 601/2 |
| 6,626,855 B1 | 9/2003 | Weng et al. | 601/3 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,716,184 B2 | 4/2004 | Vaezy et al. | 601/3 |
| 6,719,699 B2 | 4/2004 | Smith | 600/459 |
| 6,735,461 B2 | 5/2004 | Vitek et al. | 600/411 |
| 6,846,291 B2 | 1/2005 | Smith et al. | 600/459 |
| 7,285,093 B2 | 10/2007 | Anisimov et al. | 600/437 |
| 2002/0016557 A1 | 2/2002 | Duarte et al. | 601/2 |
| 2002/0193681 A1 | 12/2002 | Vitek et al. | 600/411 |

(Continued)

FOREIGN PATENT DOCUMENTS

EP    01265223 B1    11/2002

OTHER PUBLICATIONS

Vaezy (1999) Hemostasis using high intensity focused ultrasound, Eur. J. Ultrasound, vol. 9, No. 1, pp. 79-87.*

(Continued)

*Primary Examiner*—Jon P Weber
*Assistant Examiner*—Samuel W Liu
(74) *Attorney, Agent, or Firm*—Ronald M. Anderson

(57) ABSTRACT

Selective occlusion of a blood vessel is achieved by selectively damaging endothelial cells at a target location in the blood vessel, resulting in the formation of a fibrin clot proximate to the damaged endothelial cells. Additional fibrinogen can then be introduced into the blood vessel if occlusion is not achieved, as the fibrinogen is converted to fibrin by enzymes released by the exposed thrombogenic tissue and activated platelets. Endothelial cells are selectively damaged using thermal effects induced by ultrasound, by mechanical effects induced by ultrasound, or by mechanical effects produced by a tool introduced into the blood vessel (such as a catheter-based tool). A particularly preferred technique for selectively damaging endothelial cells involves introducing an ultrasound activatable agent into the blood vessel, and causing cavitation in that agent using pulses of high-intensity focused ultrasound having a duration insufficient to induce thermal damage in adjacent perivascular tissue.

25 Claims, 9 Drawing Sheets

U.S. PATENT DOCUMENTS

| | | | |
|---|---|---|---|
| 2002/0193831 A1 | 12/2002 | Smith, III | 607/2 |
| 2003/0018255 A1 | 1/2003 | Martin et al. | 600/437 |
| 2003/0069569 A1 | 4/2003 | Burdette et al. | 606/27 |
| 2003/0125623 A1 | 7/2003 | Kelly et al. | 600/437 |
| 2004/0019278 A1 | 1/2004 | Abend | 600/545 |
| 2004/0030268 A1 | 2/2004 | Weng et al. | 601/2 |
| 2004/0078034 A1 | 4/2004 | Acker et al. | 606/27 |
| 2004/0097805 A1 | 5/2004 | Verard et al. | 600/428 |
| 2004/0097840 A1 | 5/2004 | Holmer | 601/2 |
| 2004/0143186 A1 | 7/2004 | Anisimov et al. | 600/437 |
| 2004/0153126 A1 | 8/2004 | Okai | 607/1 |
| 2004/0181178 A1 | 9/2004 | Aldrich et al. | 601/3 |
| 2004/0234453 A1 | 11/2004 | Smith | 424/9.5 |
| 2004/0254620 A1 | 12/2004 | Lacoste et al. | 607/96 |

OTHER PUBLICATIONS

Hwang et al. (2005) Vascular effects induced by combined 1-MHz ultrasound and microbubble contrast agent treatments in vivo, Ultrasound Med. Bio., vol. 31, No. 4, pp. 553-564.*

Rosen et al. (2000) "Vascular occlusive disease", pp. 1-37.*

Idell et al. ( 2001) Fibrin turnover in lung inflammation and neoplasia, Am. J. Respir. Crit .Care Med., vol. 163, No. 2, pp. 578-584.*

Bachmann et al. (2006) Targeting mucosal addressin cellular adhesion molecule (MAdCAM)-1 to noninvasively image experimental Crohn's disease, Gastroenterology, vol. 130, No. 1, pp. 8-16.*

Chong et al. (2003) Tissue factor and thrombin mediate myocardial ischemia-reperfusion injury, Ann. Thorac. Surg., vol. 75, No. 2, pp. S649-S655.*

Bokarewa et al. (2002) Tissue factor as a proinflammatory agent, Arthritis Res., vol. 4, No. s, pp. 190-195.*

Vaezy et al. (2005) Intra-operative acoustic hemostasis of liver: production of a homogenate for effective treatment, Ultrasonics, vol. 43, No. 4, pp. 265-269.*

Miller et al. (2000) Diagnostic ultrasound activation of contrast agent gas bodies induces capillary rupture in mice, Proc. Natl. Acad. Sci. U S A, vol. 97, No. 18, pp. 10179-10184.*

Ewert et al. (1992) Anti-myeloperoxidase antibodies stimulate neutrophils to damage human endothelial cells, Kidney Int., vol. 41, No. 2, pp. 375-383.*

UltraSound TIP (2007, updated) http://www.us-tip.com/serv1.php?type=db1&dbs=Cavitation, p. 1.*

American Red cross (2007, updated) "Blood 101", http://web.redcrossblood.org/portal/GA/rc/bloodfacts/index_blood_facts.asp, pp. 1-4.*

Williamson et al. (1996) Color Doppler ultrasound imaging of theeye and orbit, Survey Ophthalmol., vol. 40, issue 4, pp. 255-267.*

Merriam-webster Dictionary (2008, updated) www.merriam-webster.com/dictionary/desired, p. 1.*

Anand, Ajay et al. "Using the ATL 1000 to Collect Domodulated RF Data for Monitoring HIFU Lesion Formation." Center for Industrial and Medical Ultrsound, University of Washington. Abstract. 11pp.

Bauer, A.; Solbiati, L.; Weissman, N. "Ultrasound Imaging with SonoVue: Low Mechanical Index Real-time Imaging." Acad Radiol 2002, 9(suppl 2):S282-S284.

Hatangadi, Ram Bansidhar. "A Novel Dual Axis Multiplanar Transesophageal Ultrasound Probe for Three-Dimensional Echocardiograph." University of Washington, Department of Sciences and Engineering. (1994), Abstract. vol. 55-11B: 1pg.

Indman, Paul, MD,. "Alternatives in Gynecology." Hysteroscopy © 2000 OBGYN.net <http://www.gynalternatives.com/hsc.html>.

Kaczkowski, Peter J., Vaezy, Shahram, Martin, Roy, Crum, Lawrence. "Development of a High Intensity Focused Ultrasound System for image-guided ultrasonic surgery." Ultrasound for Surgery 2001. <http://cimu.apl.washington.edu/hifusurgerysystem.html>.

Klibanov, Alexander L; Rasche, Peter T.; Hughes, Michael S.; Wojdyla, Jolette K.; Galen, Karen P.; Wiblee, James H.; Brandenburger, Gary H.. "Detection of Individual Microbubbles of an Ultrasound contrast Agent: Fundamental and Pulse Inversion Imaging[1]." Acad Radiol 2002, 9(suppl 2):S279-S281.

Ostensen, Jonny, PhD; Bendiksen, Ragner, MSc. "Characterization and Use of Ultrasound Contrast Agents." Acad Radiol 2002; 9(suppl 2):S276-S278.

Owaki, T., Nakano, S. Arimura, K., Aikou, T. "The Ultrasonic Coagulating and Cutting System Injuries Nerve Function." First Department of Surgery, Kagoshima University School of Medicine, Kagoshima, Japan, Endoscopy. (2002) 575-579.

Physicians. "Breast Cancer—Insightec: focused ultrasound for non invasive treatment." FAQ <http://www.exablate2000.com/physicians_faq.html>.

Tardy, I.; Pochon, S.; Theraulaz, P. Nanjappan; Schneider, M. "In Vivo Ultrasound Imaging of Thrombi Using a Target-specific Contrast Agent[1]." Acad Radiol 2002, 9(suppl 2):S294-S296.

Vaezy, Shahram et al. 2001. "Acoustic surgery." Physics World (August): 35-39.

Vaezy, Shahram et al. 2001. "Experimental Investigations and Device Development." First International Workshop on the Application of HIFU in Medicine. (May 10-13): 4pp.

Watkin, Kenneth L., PhD; McDonald, Michael A., BS. "Multi-Modal Contrast Agents: A First Step[1]." Acad Radiol 2002, 9(suppl 2):S285-S287.

Watkin, Kenneth L., PhD; McDonald, Michael A., BS. "Schematic of the Tube, Cross Section Ultrasound Images of the Tube With Different Contrast Media (CM)." Acad Radiol 2002, 9(suppl 2):S288-S289.

Physicians. "Breast Cancer—Insightec: focused ultrasound for non invasive treatment." FAQ <http://www.exablate2000.com/physicians_faq.html>, [downloaded from the internet on Oct. 14, 2004].

Yu, T., Wang, G., Hu, K., Ma, P., Bai, J., and Wang, Z. "A microbubble agent improves the therapeutic efficiency of high intensity focused ultrasound: a rabbit kidney study." (Abstract) NDN 234-0481-1539-3. Urol Res. Feb. 2004; 32(1): 14-9. Epub Dec. 4, 2003.

Wickline, Samuel A., MD; Hughes, Michael, PhD; Ngo, Francis C., MD; Hall, Christopher, S., PhD; Marsh, Jon, N., PhD; Brown, Peggy A; Allen, John S., BS; McLean, Mark D.; Scott, Michael J., BS; Fuhrhop, Ralph W.; Lanza, Gregory M., MD, PhD. "Blood Contrast Enhancement with a Novel, Non-Gaseous Nanoparticle Contrast Agent[1]," Acad Radiol 2002, 9(suppl 2):S290-S293.

Rivens, I.H., Rowland, I.J., Denbow, M., Fisk, N.M., Harr, G.R., Leach, M.O. "Vascular occlusion using focused ultrasound surgery for use in fetal medicine." European Journal of Ultrasound 9 (1999): 89-97.

Tachibana, Katsuro and Shunro MD., PhD. "The Use of Ultrasound for Drug Delivery." First Department of Anatomy, Fukuoka University School of Medicine, Nanakuma, Japan,Echocardiography. (2001) 323-328.

Ka-yun Ng, Yang Liu, "Therapeutic Ultrasound: Its Application in Drug Delivery." Medicinal Research Reviews, vol. 22, 204-223, 2002 © 2002 John Wiley & Sons, Inc.

Porter, T.R., Xie, F. "Ultrasound, Microbubbles and Thrombolysis." Progress in Cardiovascular Diseases, vol. 44, No. 2, Oct. 2001: 101-110.

Nobuki Kudo, Takehiro Miyaoka, Kengo Okada, and Katsuyuki Yamamoto. "Study on Mechanism of Cell Damage Caused by Microbubbles Exposed to Ultrasound." Graduate School of Engineering, Hokkaido University, Japan, Research Institute for Electronic Science, Hokkaido University, 060-0812 Japan.

Holt, Glynn, R., Roy, Ronald, A., Edson, Patrick A., Yang, Xinmai. "Bubbles and Hifu: the Good, the Bad and the Ugly." Boston University, Department of Aerospace and Mechanical Engineering, Boston, MA 02215: 120-131.

Everbach, Carr, E. and Charles W. Francis. "Cavitational Mechanisms in Ultrasound-Accelerated Thrombolysis at 1 MHz." Ultrasound in Med. & Biol., vol. 26, No. 7, pp. 1153-1160, 2000. Copyright 2000 World Federation in Medicine and Biology.

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305-1320, 1999. Copyright 1999 World Federation for Ultrasound in Medicine & Biology.

Poliachik, Sandra L., et al. "Effect of High-Intensity Focused Ultrasound on Whole Blood with or without Microbubble Contrast Agent." Ultrasound in Med. & Biol., vol. 25, No. 6, 1999: 991-998.

Poliachik, Sandra L., et al. "Activation, Aggregation and Adhesion of Platelets Exposed to High-Intensity Focused Ultrasound." Ultrasound in Med. & Biol., vol. 27, No. 11, pp. 1567-1576, 2001.

Rosenschein, Uri, et al. "Ultrasound Imaging-Guided Nonivasive Ultrasound Thrombolysis-Preclinical Results." © 2000 American Heart Association, Inc. (Circulation. 2000;102:238-245.) <http://www.circulationaha.com.org>.

Tachibana, Katsuro, and Shunro M.D., Ph.D. "Albumin Microbubble Echo-Contrast Material as an Enhancer for Ultrasound Accelerated Thrombolysis." (Circulation, 1995; 92: 1148-1150.) © 1995 American Heart Association, Inc.

Miller, Morton W. et al. "A Review of In Vitro Bioeffects of Intertial Ultrasonic Cavitation From a mechanistic Perspective." Ultrasound in Med & Biol., vol. 22, No. 9, pp. 1131-1154, 1996.

Rosenchein, Uri, et al. "Shock-Wave Thrombus Ablation, A New Method for Noninvasive Mechanical Thrombolysis." The American Journal of Cardiology, vol. 70, Issue 15, Nov. 1992: pp. 1358-1361.

Guzman, Hector R., et al. "Ultrasound-mediated disruption of cell membranes. II. Heterogeneous effects on cells." J. Acoust. Soc. Am 110 (1), Jul. 2001: pp. 597-606.

Guzman, Hector R., et al. "Ultrasound-Mediated Disruption of Cell Membranes. I. Quantification of Molecular uptake and Cell Viability." J. Acoust. Soc. Am. 110 (1), Jul. 2001: pp. 588-595.

Hynynen, Kullervo, et al. "Potential Adverse Effects of High-Intensity Focused Ultrasound Exposure on Blood Vessels in Vivo." Ultrasound in Med. & Biol., vol. 22, No. 2, 193-201, 1996.

Chen, Wen-Shiang, et al. "A comparison of the fragmentation thresholds and inertial cavitation doses of different ultrasound contrast agents." J. Acoust. Soc. Am. 113 (1), Jan. 2003: pp. 643-651.

Dayton, Paul, A., et al. "The magnitude of radiation force on ultrasound contrast agents." J. Acoust. Soc. Am. 112 (5) Pt. 1, Nov. 2002: pp. 2183-2192.

"Mechanical Bioeffects in the presence of gas-carrier ultrasound contrast agents." J Ultrasound Med. 19: 120-142, 2000.

Chen, Wen-Shiang, et al. "Inertial Cavitation Dose and Hemolysis Produced in Vitro with or Without Optison." Ultrasound in me. & Biol., vol. 29, No. 5, pp. 725-737, 2003.

* cited by examiner

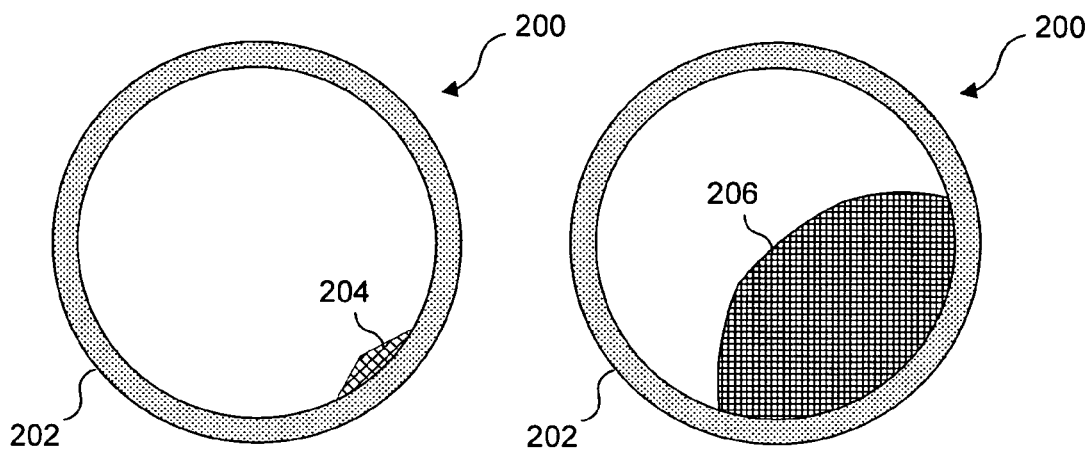
*FIG. 9A*  *FIG. 9B*
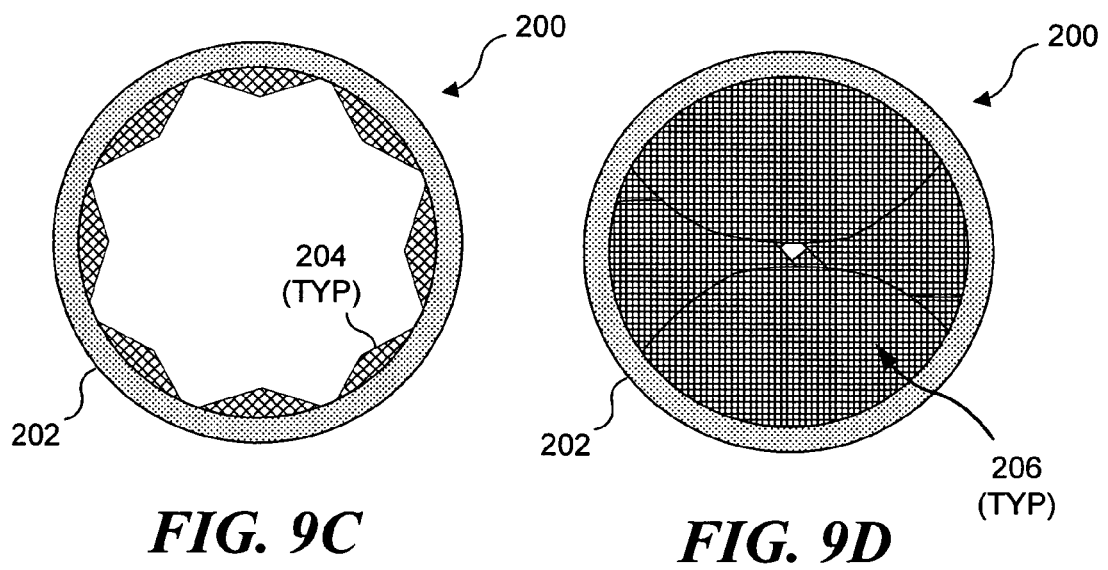
*FIG. 9C*  *FIG. 9D*

ULTRASOUND TARGET VESSEL OCCLUSION USING MICROBUBBLES

This invention was made with U.S. Government support under grants 1F32DK65413-01 and 8R01-EB00350-02 awarded by the National Institutes of Health, and U.S. Army Contract No. DAMD17-02-2-0014, awarded by the Department of Defense. The U.S. Government has certain rights in the invention.

FIELD OF THE INVENTION

The present invention generally relates to selectively occluding blood flow in a vessel, and more specifically, to a method of selectively occluding blood flow by damaging endothelial cells at a portion of the blood vessel in which an occlusion is desired, and then introducing fibrinogen into the blood vessel.

BACKGROUND OF THE INVENTION

While it is widely recognized that reduction of blood flow in arties is a major factor in heart disease, there are many medical conditions in which restricting or occluding blood flow through a blood vessel is desirable. For example, sclerotherapy is the injection of a sclerosing agent (such as morrhuate sodium) into a blood vessel to produce inflammation and scarring; injection of the sclerosing agent closes the lumen, and is followed by shrinkage and hardening of the vessel. Sclerotherapy is often used to treat varicose veins.

Yet another medical condition for which occluding blood flow is an effective therapy is cirrhosis, which can lead to the development of esophageal and gastric varices. When portal venous flow becomes obstructed (for example, in cirrhosis of the liver, distorted hepatic sinusoids restrict the flow of blood through the liver), varices can develop, creating a collateral circuit that 'bypasses' the portal venous system and returns blood to the systemic circulation. A high rate of bleeding is associated with such varices, often leading to increased morbidity. Improving survival in patients with cirrhotic livers may provide such patients with additional time necessary to obtain a more definitive therapy, such as a liver transplant. Current methods for preventing bleeding from such varices include the use of non-selective beta-blockers and/or nitrates, endoscopic therapy (band ligation or injection therapy), transjugular intrahepatic portosystemic shunts, or surgical decompression of the portal venous system. Injection therapy is based on introducing a sclerosant agent into the vessel. Such agents cause local irritation to the vessel, resulting in rapid intravascular thrombus formation. Although injection therapy is effective in occluding vessels and arresting active bleeding, ulceration of the mucosa and bacteremia are common side effects, and there is potential for serious complications, such as perforation, acute respiratory distress syndrome (ARDS), and thromboembolic events.

In the United States, the most common cause of cirrhosis is a hepatitis C infection. It is estimated that well over 4 million Americans have been infected with the hepatitis C virus. Since the hepatitis C infection is a chronic infection that progresses over decades, the prevalence of cirrhosis due to hepatitis C infection is expected to increase in years to come. Some projections estimate that the number of cases of cirrhosis due to the hepatitis C will increase from about 450,000 in 2000 to almost 900,000 by the year 2020. Studies indicate that 60-90% of patients who develop cirrhosis go on to develop esophageal and/or gastric varices. Of patients who develop varices, 30-40% have bleeding that is attributed to varices. Of those patients who experience variceal bleeding, 20-35% will die as a result of their initial variceal bleed, and, of those who survive, 70% will experience a recurrent episode of variceal bleeding within one year. Clearly, variceal bleeding is a major cause of morbidity and mortality in patients with cirrhosis, and it would be desirable to provide new therapies that can be used to selectively occlude blood flow in a blood vessel, and thus, to treat variceal bleeding and other medical conditions (such as varicose veins).

Ultrasound has gained acceptance as an imaging technique particularly well suited to providing information about a patient's internal structures without risk of exposure to potentially harmful radiation, as may occur when using X-ray imaging techniques. While often used as an imaging tool, at higher intensities, ultrasound can induce biological effects (bioeffects), including thermal effects and mechanical effects. The thermal effects are generally the result of the absorption of acoustic energy, and the mechanical effects are generally based on the cavitation produced by gas-filled bubbles. Several different medical therapies that are based on the bioeffects of ultrasound have been studied. Because ultrasound can pass through tissue, ultrasound is generally non-invasive, and non-invasive/minimally invasive therapies are growing in popularity. Advantages of such non-invasive/minimally invasive therapies include reduced blood loss, reduced risk of infection, shorter hospital stays, and generally lower health care costs.

One ultrasound therapy that has been investigated is the use of high intensity focused ultrasound (HIFU) to destroy abnormal tissue and to stop bleeding. While HIFU has been shown to be effective in arresting bleeding and occluding vessels, significant thermal injury to perivascular tissue often results from such therapy. While there are certainly medical conditions where such tissue damage is acceptable (for example, to stop bleeding in trauma victims, since the failure to stem blood loss will result in death), such damage is likely to be unacceptable for the treatment of varicose veins and varices as discussed above. It would therefore be desirable to provide an ultrasound based minimally invasive therapy for occluding blood flow in vessels with minimal damage to adjacent tissue. Such a therapy can be employed for hemostasis and sclerotherapy.

SUMMARY OF THE INVENTION

The present invention is directed to a method for selectively occluding a blood vessel by damaging endothelial cells at a target location in the blood vessel. Where such damage exposes thrombogenic tissue underlying the endothelial cells, a relatively small fibrin clot will form proximate the damaged endothelial cells. Generally, the resulting fibrin clot will not be sufficiently large to achieve a meaningful occlusion of the blood vessel. To enlarge the fibrin clot formed proximate the damaged endothelial cells, additional fibrinogen is introduced into the blood vessel. While fibrinogen is present in relatively small amounts in normal blood vessels, increasing the amount of fibrinogen in the blood vessel will result in the expansion of the original relatively small fibrin clot, as fibrinogen is converted to fibrin by enzymes released by the exposed thrombogenic tissue and activated platelets attracted to the exposed thrombogenic tissue. Because fibrinogen is blood soluble and is inert until activated by enzymes released by activated platelets and exposed thrombogenic tissue, the fibrinogen can be introduced directly into the blood vessel in question (by injection through the skin or delivered via a catheter, depending on the location of a blood vessel), or the fibrinogen can be introduced systemically (via an intravenous injection into another more readily accessible blood vessel).

Several different techniques can be used to selectively damage the endothelial cells at a target location where an occlusion is desired. As will be discussed in greater detail below, in a particularly preferred embodiment of the present invention, the endothelial cells are damaged by using a short pulse of HIFU to induce cavitation proximate the target location. Cavitation is an energetic phenomenon, which will result in mechanical damage to the endothelial cells proximate the cavitation sites. This technique has the benefit of substantially eliminating thermal damage to perivascular tissue. It should be understood however, that other techniques can be used to selectively damage endothelial cells proximate the target location.

For example, a catheter can be inserted into the blood vessel and advanced to the target location. An expandable member portion of the catheter is then inflated such that the endothelial tissue contacted by the expandable member is damaged. If desired, the surface of the expandable member can be made abrasive, such that contact between the expandable member and that the endothelial cells abrades the endothelial cells to expose the highly thrombogenic tissue underlying the endothelial cells. Alternatively, an abrasion tool can be inserted into the catheter and advanced out from a distal tip of the catheter to similarly abrade or otherwise damage endothelial cells proximate target location, to expose the underlying highly thrombogenic tissue.

While endothelial cells certainly can be selectively damaged using a catheter, using ultrasound facilitates a less invasive technique to be achieved, because ultrasound waves can pass through tissue. Depending on the location of the blood vessel, the ultrasound transducer may be able to be disposed outside of the body entirely. Other blood vessels can be reached by ultrasound transducers disposed within body cavities that can be accessed non-invasively, such as the rectum, vagina, esophagus or stomach.

Several different ultrasound based techniques can be used to selectively damage endothelial cells. HIFU can be used to induce thermal effects and mechanical effects. The thermal effects are based on the absorption of acoustic energy by tissue, and the mechanical effects are based on cavitation. When HIFU is used to damage endothelial cells using thermal effects, it is likely that the thermal damage will extend into the perivascular tissue adjacent to the damaged endothelial cells. While there may be cases in which such perivascular tissue damage is acceptable, exploiting the mechanical effects applied to resulting from cavitation facilitates techniques for damaging endothelial cells without also damaging adjacent perivascular tissue. One prior art technique described in U.S. Pat. No. 5,827,204 (the specification and drawings of which are hereby specifically incorporated herein by reference) employs a multi-frequency ultrasound wave for causing vaporous cavitation bubbles in a small focal zone. A relatively low frequency ultrasound signal is used to control the growth of cavitation bubbles, while a relatively high frequency ultrasound signal is used to spatially control the region in which cavitation takes place. The implosion of the cavitation bubbles adjacent to endothelial tissue is believed to transfer energy to the tissue that damages it. This technique can be used to selectively damage endothelial cells, by causing cavitation in the blood vessel at a spatial region corresponding to the target location. The mechanical damage caused by cavitation is not likely to extend into the adjacent perivascular tissue.

A particularly preferred technique for selectively damaging endothelial cells in a blood vessel involves introducing an ultrasound activatable agent into the blood vessel, and using HIFU to activate the ultrasound activatable agent in a very well-defined spatial region corresponding to the target location. The ultrasound activatable agent disposed in portions of the blood vessel not corresponding to the focal region of the HIFU beam will not be activated, thus the cavitational damage will be limited to the portion of the blood vessel corresponding to the focal region of the HIFU beam. A useful ultrasound activatable agent are microbubbles, and ultrasound contrast agents represent particularly preferred types of the microbubbles. Because the ultrasound activatable agent will only be activated in the focal region of the HIFU beam, the ultrasound activatable agent can be introduced into the blood vessels systemically, or directly into the blood vessel in question (for example, by direct injection or using a delivery catheter). Significantly, only a very short burst of HIFU is required to activate such ultrasound activatable agents, which means that the duty cycle can be made to be of sufficiently short duration that a negligible amount of acoustic energy is absorbed by tissue in the focal region of the HIFU beam. Thus, even if some perivascular tissue lies within the focal region of the HIFU beam, no (or minimal) thermal damage will occur to the perivascular tissue, because the HIFU beam will not be energized long enough for the perivascular tissue to absorb enough acoustic energy to damage the perivascular tissue.

As noted above, once the endothelial cells proximate the target location are damaged using one of the techniques noted above, or some other technique, a relatively small fibrin clot will form proximate the damaged endothelial cells. Additional fibrinogen introduced into the blood vessel will be converted into fibrin, thereby enlarging the original fibrin clot and occluding the blood vessel.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 (prior art) schematically illustrates a normal blood vessel, including intact endothelial cells lining the blood vessel and isolating the blood flow from the highly thrombogenic tissue underlying the endothelial cells;

FIG. 2 (prior art) schematically illustrates thrombosis in a blood vessel, including damaged endothelial cells, the thrombus occurring proximate the damaged endothelial cells;

FIG. 3 (prior art) schematically illustrates a coagulation cascade responsible for the thrombosis illustrated in FIG. 2;

Figure 5A:
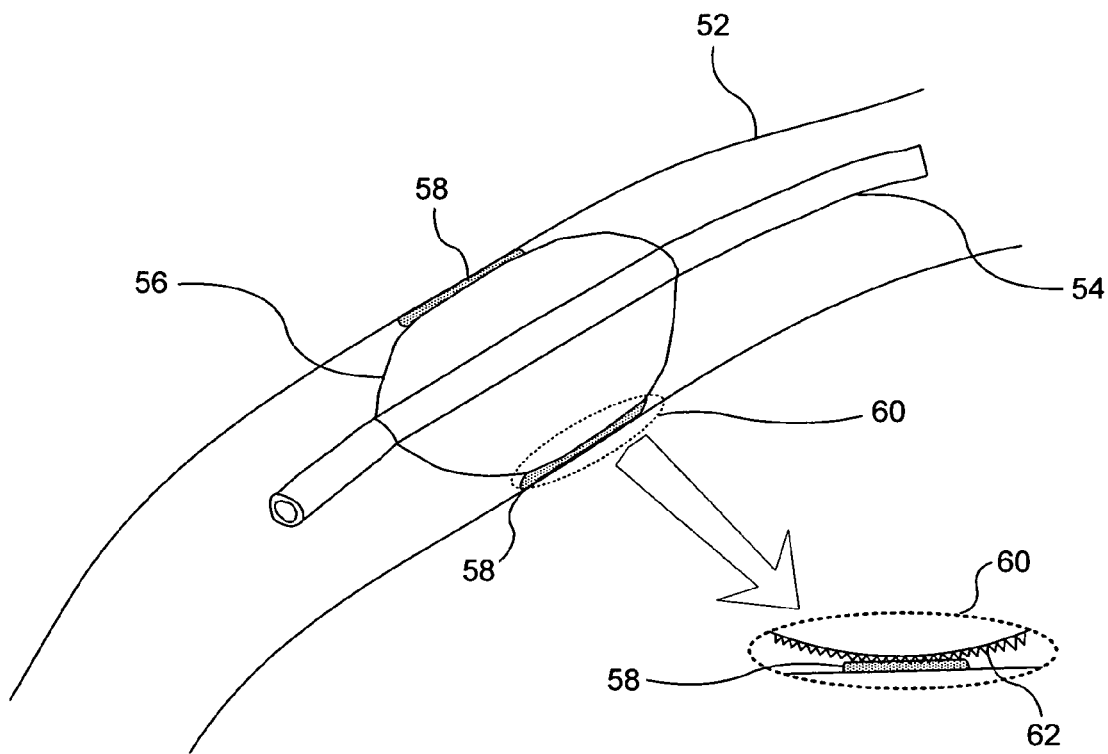
Figure 5B:
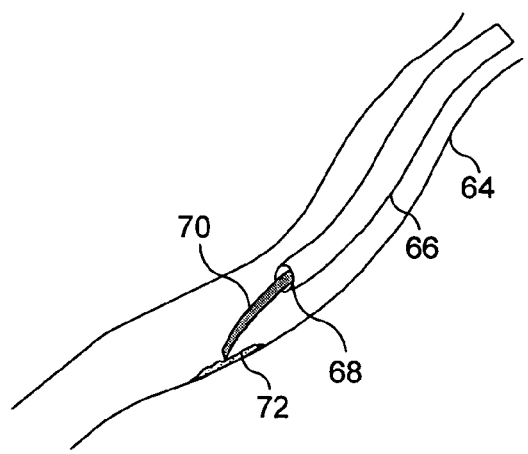
Figure 6A:
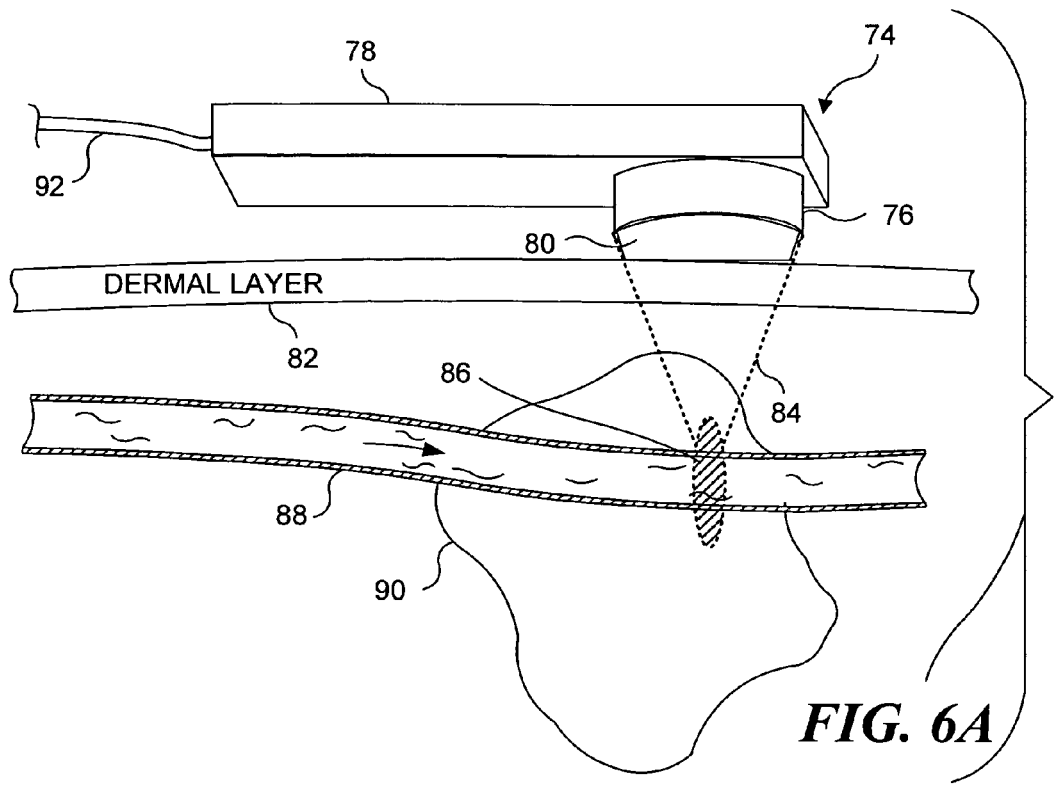
Figure 6B:
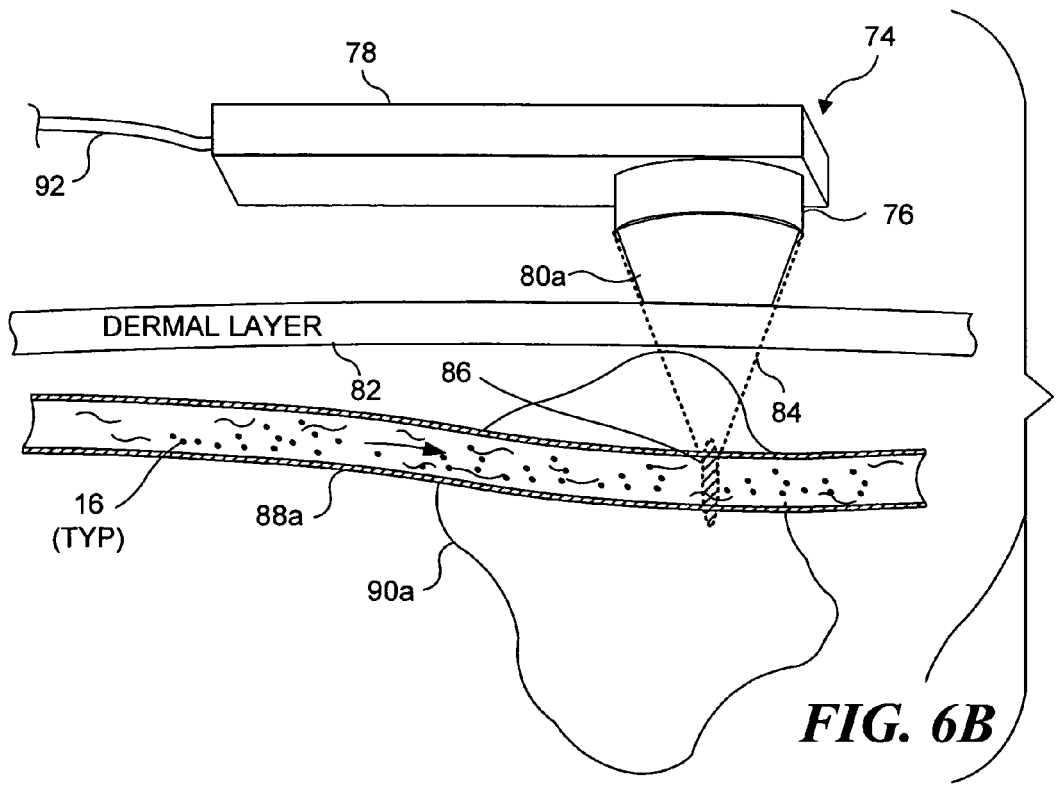
Figure 7A:
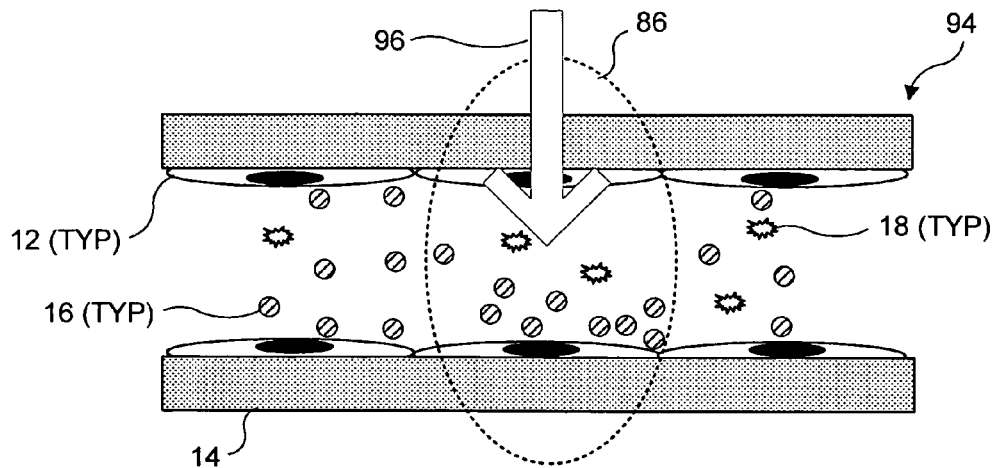
Figure 7B:
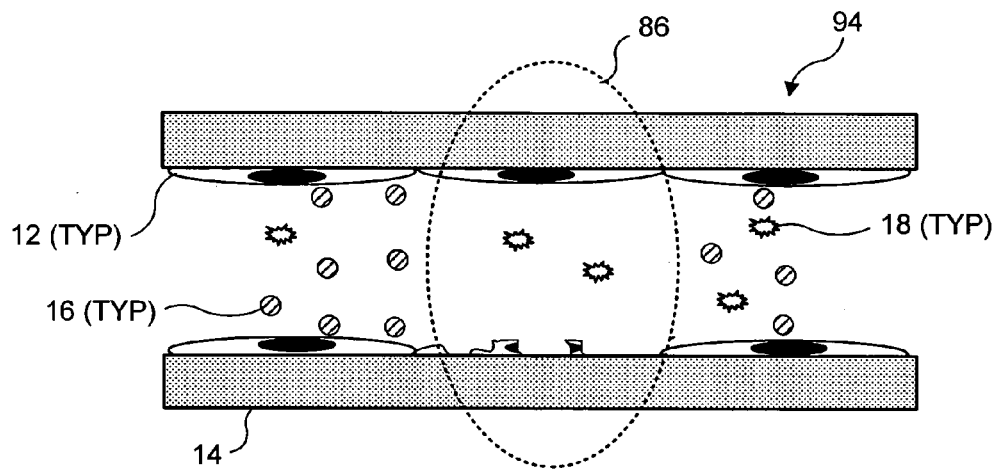
Figure 7C:
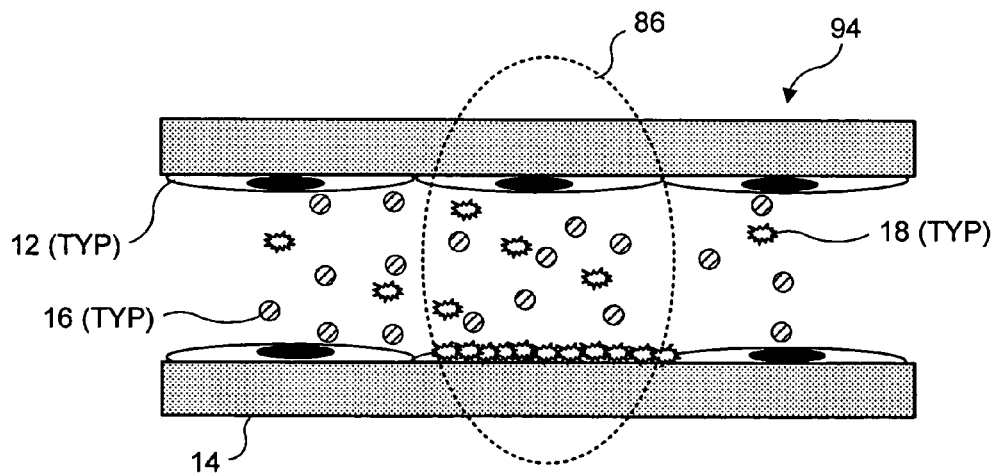
Figure 7D:
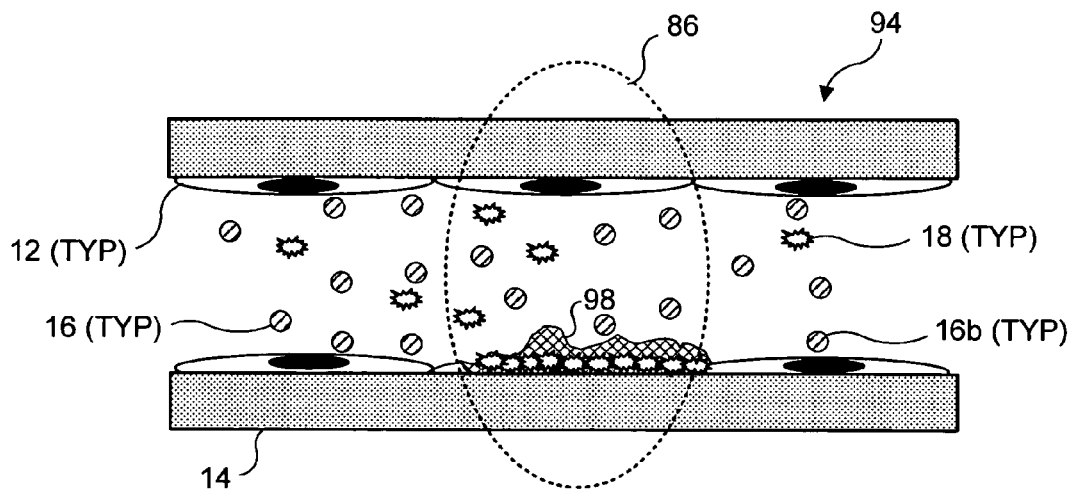
Figure 7E:
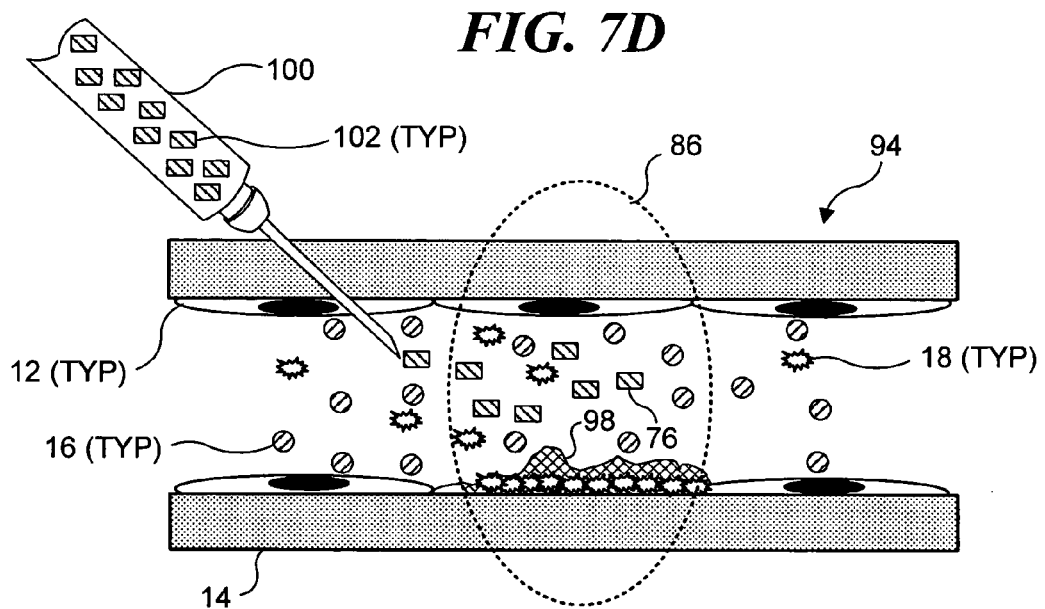
Figure 7F:
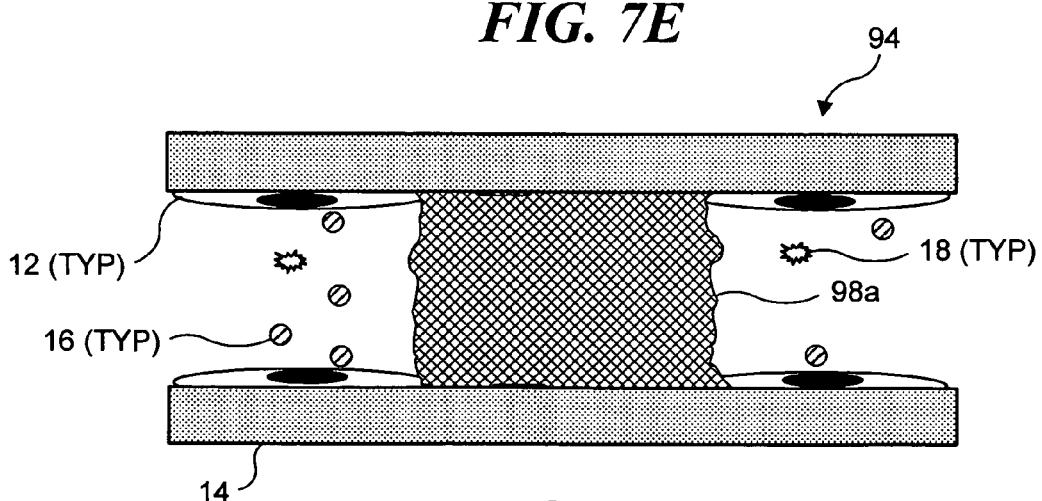
Figure 8:
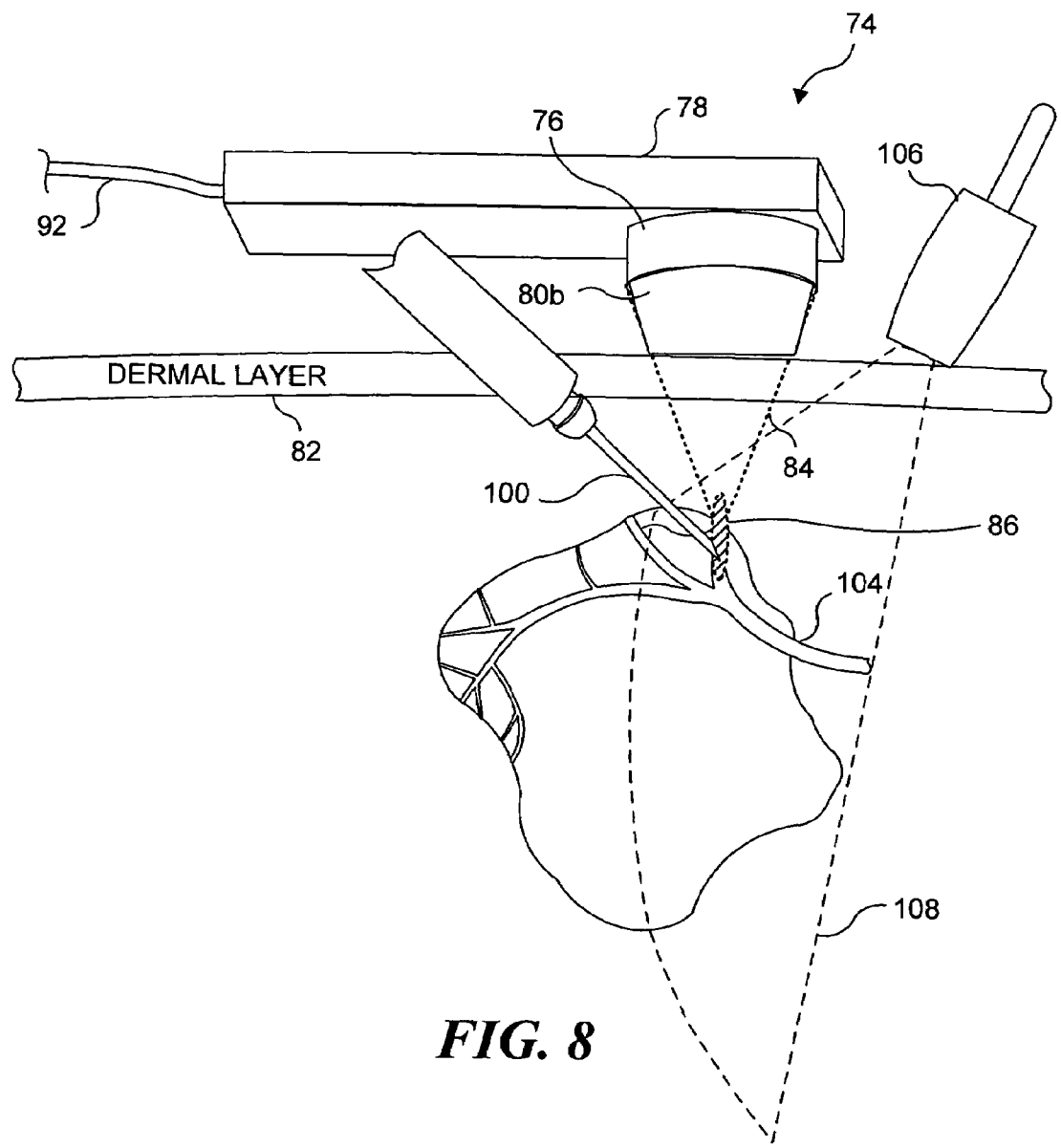

FIG. 5A schematically illustrates a balloon catheter being employed to selectively damage endothelial cells in a blood vessel;

FIG. 5B schematically illustrates a catheter-based tool being employed to selectively damage endothelial cells in a blood vessel;

FIG. 6A schematically illustrates a HIFU therapy probe being employed to selectively damage endothelial cells in a blood vessel;

FIG. 6B schematically illustrates a HIFU therapy probe and ultrasound activatable agent being employed in combination to selectively damage endothelial cells in a blood vessel;

FIG. 7A schematically illustrates a blood vessel, including intact endothelial cells and ultrasound activatable agent;

FIG. 7B schematically illustrates the blood vessel of FIG. 7A after HIFU has been used to selectively activate the ultrasound activatable agent in a portion of the blood vessel, resulting in damage to the endothelial cells lining the blood vessel in that portion;

FIG. 7C schematically illustrates the blood vessel of FIG. 7B after platelets naturally present in the blood vessel have been attracted to the damaged endothelial cells and exposed thrombogenic tissue;

FIG. 7D schematically illustrates the blood vessel of FIG. 7C after the generation of a thrombus proximate the damaged endothelial cells;

FIG. 7E schematically illustrates the blood vessel of FIG. 7D after the introduction of additional fibrinogen;

FIG. 7F schematically illustrates the blood vessel of FIG. 7E after a portion of the additional fibrinogen has been converted to fibrin, thereby enlarging the thrombus and occluding the blood vessel;

FIG. 8 schematically illustrates a HIFU therapy probe and an ultrasound imaging probe being employed to achieve image guided HIFU-based occlusion of a blood vessel in accord with the present invention; and FIGS. 9A-9D schematically illustrate a method for occluding a blood vessel by damaging endothelial cells disposed about the circumference of the blood vessel, without requiring the contemporaneous introduction of fibrinogen or thrombin.

DESCRIPTION OF THE PREFERRED EMBODIMENT

Overview of the Present Invention

As noted above, the present invention can be used to selectively occlude a blood vessel by selectively damaging endothelial cells in a portion of a blood vessel where an occlusion is desired. The damage to the endothelial cells exposes underlying tissue, which releases enzymes causing naturally occurring fibrinogen to polymerize, thereby depositing a fibrin clot along the vessel wall. Additional fibrinogen is introduced into the blood vessel. The additional fibrinogen is similarly converted to fibrin, enlarging the clot. An advantage of the present invention is that because the thrombus is formed on the underlying tissue where damage was caused to the endothelial tissue, the clot that is produced cannot readily break loose from that site and cause undesirable problems in other parts of the body, e.g., by occluding a blood vessel in a patient's brain. While a number of different techniques can be used to selectively damage the endothelial cells, in at least one embodiment, cavitation is induced in an ultrasound activatable agent using HIFU. While imaging ultrasound can induce cavitation of ultrasound contrast agents, the lower energy imaging ultrasound (as compared to higher energy HIFU) is unlikely to induce cavitation energetic enough to damage the endothelium. Before discussing embodiments of the present invention in detail, it may be useful to review thrombosis, cavitation, and HIFU in general.

Thrombosis

Thrombosis is defined as the formation of a clotted mass of blood within a blood vessel. It is a complex process that involves the interaction of platelets, red blood cells, inflammatory cells, circulating clotting factors, and the vessel wall. The role of endothelial cells and the clotting cascade are discussed briefly below.

Figure 1:
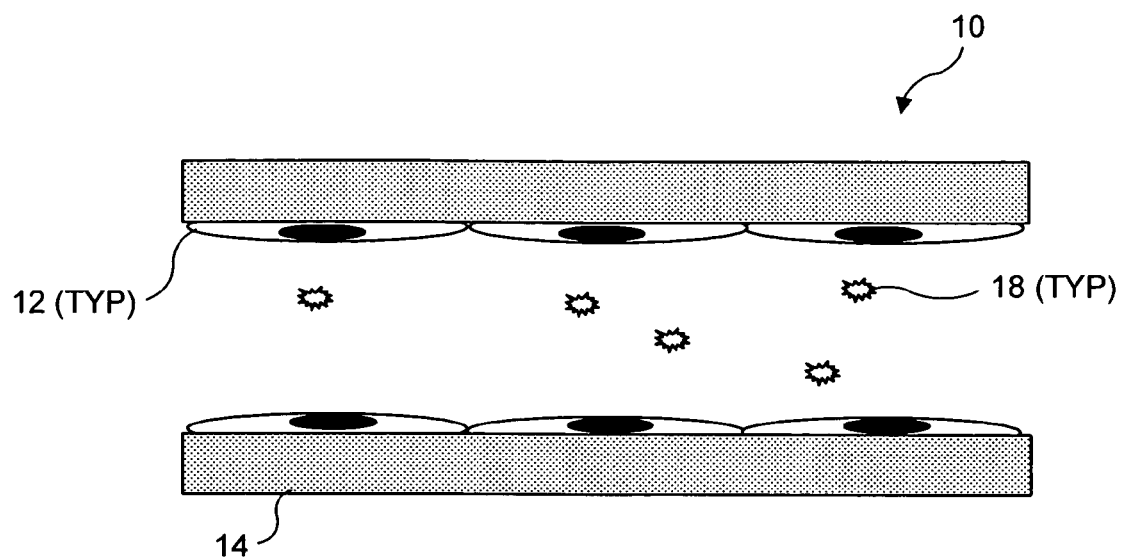
Figure 3:
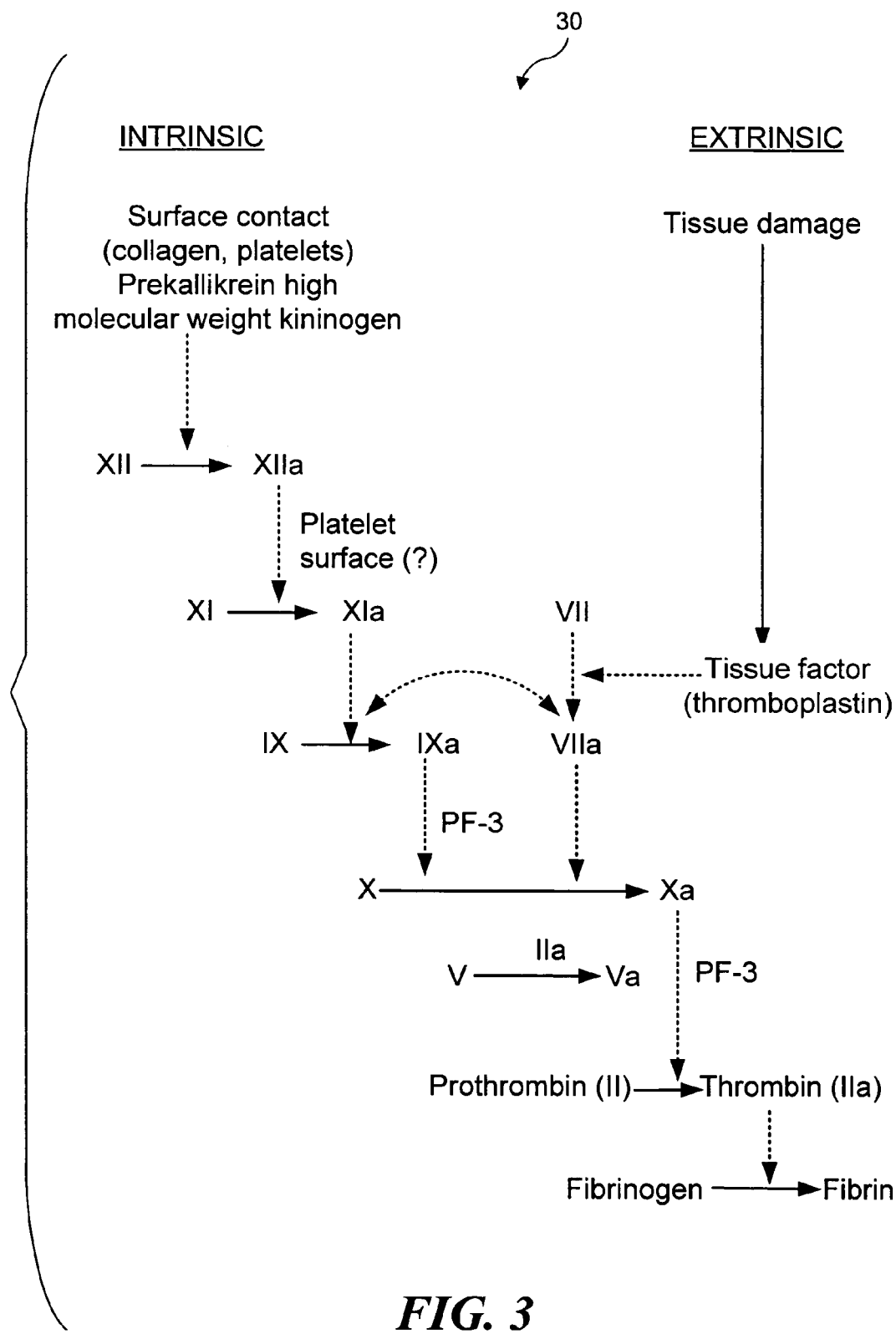

FIG. 1 (prior art) schematically illustrates a normal blood vessel 10, lined with healthy endothelial cells 12. A basement membrane 14 underlying endothelial cells 12 comprises highly thrombogenic sub-endothelial connective tissue. Red blood cells (not specifically shown) and platelets 18 circulate through blood vessel 10. The endothelial cells play a key role in hemostasis, because they isolate platelets 18 from the highly thrombogenic sub-endothelial connective tissue of basement membrane 14. The endothelial cells themselves are highly resistant to thrombus formation. In addition to insulating the circulating blood from the highly thrombogenic sub-endothelial connective tissue, the endothelial cells actively binds and inhibits thrombin, which is the terminal enzyme of the coagulation cascade that converts fibrinogen to fibrin. The coagulation cascade, schematically illustrated in FIG. 3 (from Cotran R S, Kumar V, Robbins S L. Robbins Pathologic Basis of Disease. 1989; $4^{th}$ edition), is well understood and need not be discussed herein in further detail. The endothelium tissue also activates proteins C and S, which are potent anticoagulants. The endothelium tissue inhibits platelet aggregation by releasing prostacyclin. Thus, healthy and intact endothelial cells inhibit thrombosis based on a variety of different mechanisms.

Figure 2:
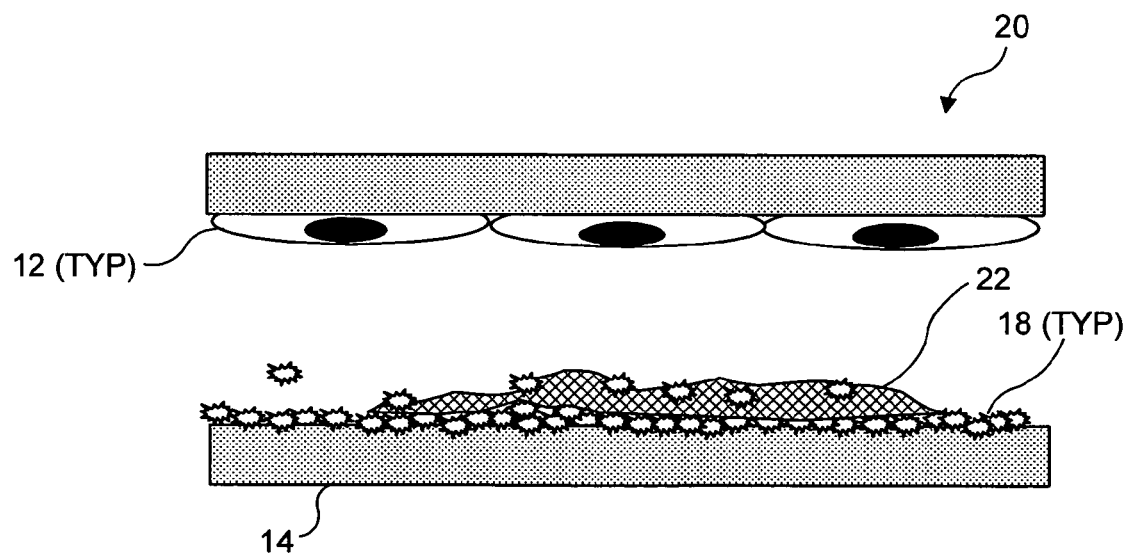

When endothelial cells are damaged, thrombus formation is promoted. FIG. 2 (prior art) schematically illustrates this process. In a blood vessel 20, endothelial cells 12 lining the upper portion of blood vessel 20 are healthy; however, the endothelial cells that should be lining the lower portion of blood vessel 20 are absent (having been damaged or destroyed). Damaged endothelial cells cause the release of tissue factor, which then activates the extrinsic clotting cascade of FIG. 3 (prior art). The damaged endothelial cells also secrete von Willebrand factor (vWF) and platelet activating factor (PAF), which activate platelets 18, causing the platelets to attach themselves to the sub-endothelial surface exposed by the damaged endothelial cells.

When endothelial cells are damaged and basement membrane 14 (and connective tissue) underlying the endothelial cells is exposed, the endothelial cells no longer insulate the circulating blood components from the highly thrombogenic sub-endothelial tissue, resulting in the initiation of thrombosis. Of the sub-endothelial components, the most thrombogenic is fibrillar collagen, which stimulates platelet adhesion and activates the intrinsic pathway of the clotting cascade.

The clotting cascade involves a complex series of transformations of proenzymes to activated enzymes, which eventually results in the formation of fibrin, an insoluble protein that then polymerizes to help stabilize a blood clot 22. The clotting cascade can be activated by the release of tissue factor from a damaged endothelial cell, activated platelets, and by the collagen of an exposed surface of sub-endothelium. Damage to the endothelial surface results in the activation of both an intrinsic coagulation pathway and an extrinsic coagulation pathway. The intrinsic pathway is activated by exposure of the damaged endothelial surface, resulting in activation of platelets that triggers the intrinsic pathway. The extrinsic pathway is triggered by the release of tissue factor from the damage that occurs to the vascular smooth muscle tissue. Both pathways result in the activation of thrombin.

The conversion of fibrinogen to fibrin by the enzymatic reaction catalyzed by thrombin represents the final step of the coagulation cascade resulting in the polymerization of fibrin. Fibrinogen is a soluble protein that is primarily synthesized by the liver, and which is present in the bloodstream. In addition, activated platelets also secrete fibrinogen. The conversion of soluble fibrinogen to the insoluble fibrin polymer results from a three step process that begins with the cleavage of fibrinogen by thrombin, resulting in a fibrin monomer. Fibrin monomers then assemble into an aggregation of fibers through non-covalent bonds. Typically, in the formation of an intravascular thrombus, platelets and erythrocytes become incorporated into the fibrin monomer aggregation. The non-covalently bound fibrin assembly then undergoes covalent stabilization by factor XIIIa-catalyzed cross-linking.

The durability of the fibrin clot depends on the balance of pro-coagulant and anticoagulant activity. Fibrin clots undergo degradation by a process termed fibrinolysis. Fibrinolysis is mediated by plasmin, a serine protease. Plasmin is similar to other proteins in the coagulation cascade requiring activation from its inactive proenzyme form, plasminogen, by tissue-type plasminogen activator (tPA). Plasminogen is a circulating plasma protein that is primarily synthesized by the liver and binds to polymerized fibrin during clot formation. Activation of plasminogen that is bound to fibrin to plasmin by tPA results in degradation of fibrin leading to clot lysis.

Fibrinolysis is inhibited by plasminogen activator inhibitor-1 (PAI-1), which is secreted by damaged endothelial cells and activated platelets. In addition, PAI-1 expression by endothelial cells is up regulated in the setting of inflammation due to effects of interleukin-1 (IL-1).

Cavitation

Cavitation can be defined as the creation or motion of a gas cavity in an acoustic field. In other words, cavitation is the oscillatory movement of a gas-filled bubble in a liquid medium exposed to an acoustic field. There are two types of cavitation. Stable cavitation refers to exposing a bubble to a low pressure acoustic field, resulting in a stable oscillation of the size of the bubble. Inertial cavitation refers to exposing a bubble to an acoustic field to cause violent oscillations of the bubble, with rapid growth of the bubble during the negative pressure phase, which eventually leads to the violent collapse and destruction of the bubble. After the collapse of the bubble, one or more daughter bubbles can be generated, and those daughter bubbles can subsequently propagate inertial cavitation activity if the acoustic conditions allow. Alternatively, the bubble may be destroyed completely without generating any daughter bubbles. Inertial cavitation can result from exposing the bubble to an acoustic field that generates broadband acoustic emissions.

An interesting phenomenon has been observed when inertial cavitation occurs proximate a solid surface. The asymmetric collapse of a bubble near such a surface can create high-velocity liquid jets, which impinge upon the surface with a force sufficient to damage even metal surfaces.

Stable cavitation may lead to a phenomenon called microstreaming (rapid movement of fluid near the bubble due to its oscillating motion). Micro-streaming can produce high shear forces close to the bubble, of sufficient magnitude to disrupt cell membranes.

One aspect of the present invention relates to selectively damaging endothelial cells within the walls of blood vessels. As discussed in greater detail below, microbubbles (i.e., comprising an ultrasound activatable agent) are introduced into the blood vessel, and ultrasound is used to induce cavitation in those bubbles.

HIFU Therapy

In comparing the differences in intensities of HIFU and diagnostic ultrasound, HIFU has significantly higher time-averaged intensities in the focal region of the ultrasound transducer. Typical diagnostic ultrasound transducers deliver ultrasound with intensities on the order of 0.1-100 mW/cm$^2$ or 0.001-3 MPa depending on the mode of imaging (B-mode, pulsed Doppler, or continuous wave Doppler). In contrast, HIFU transducers deliver ultrasound with intensities in the range of 100-4000 W/cm$^2$ to the focal region.

Many therapeutic HIFU applications rely on heat generation in the tissues proximate the focal region due to absorption of a portion of the acoustic energy delivered to the focal region. HIFU therapy can quite rapidly produce temperatures in tissue of up to 100° C., causing coagulative tissue necrosis within a few seconds. Focusing results in high intensities at a specific location and over only a small volume (e.g., a cylindrical volume of about 1 mm diameter and 9 mm length, although the exact size of the focal region depends on the transducer design). Focusing the energy avoids damaging tissue located between the transducer and the focal point, because the acoustical energy intensities are much lower outside of the focal region. The depth and width of the focus of HIFU can be adjusted based on the physical design of the transducer and the operating frequency. By changing the frequency, radius of curvature, and diameter of the transducer, the dimensions of the focus can be manipulated to provide the optimal geometry for treating various treatment sites. Therefore, a transducer can be designed for applications ranging from superficial treatment sites to tissue deep within tissue. HIFU can be used in connection with ultrasound imaging, as described in U.S. Pat. No. 6,425,867, the specification and drawings of which are hereby specifically incorporated herein by reference, such that the location of the focal region can be identified using imaging ultrasound, and the HIFU therapy delivered to the desired target location.

In addition to the thermal effects associated with HIFU, there are also several different mechanical phenomena associated with high intensities of ultrasound that are not present at lower intensities of ultrasound. These mechanical phenomena include cavitation, microstreaming, and radiation forces. Cavitation and microstreaming have been discussed above. Radiation forces are developed when a wave is either absorbed or reflected. Complete reflection produces twice the force that complete absorption does. These forces are constant if the amplitude of a wave is steady and the absorption and/or reflection are constant. If the reflecting or absorbing medium is tissue or other solid material, the force presses against the medium producing a pressure, termed radiation pressure. If the medium is a liquid and can move under pressure, then streaming results.

The terms "therapeutic transducer," "HIFU transducer," and "high intensity transducer," as used herein and in the claims that follow, all refer to a transducer that is capable of being energized to produce ultrasonic waves that are much more energetic than the ultrasonic pulses produced by an imaging transducer, and which can be focused or directed onto a discrete location, such as a treatment site in a target area to produce a desired effect on tissue at the treatment site. However, in at least one embodiment of the present invention, not all ultrasonic waves produced by such a transducer are necessarily at a high intensity, as is explained below.

Details of the Present Invention

Figure 4A:
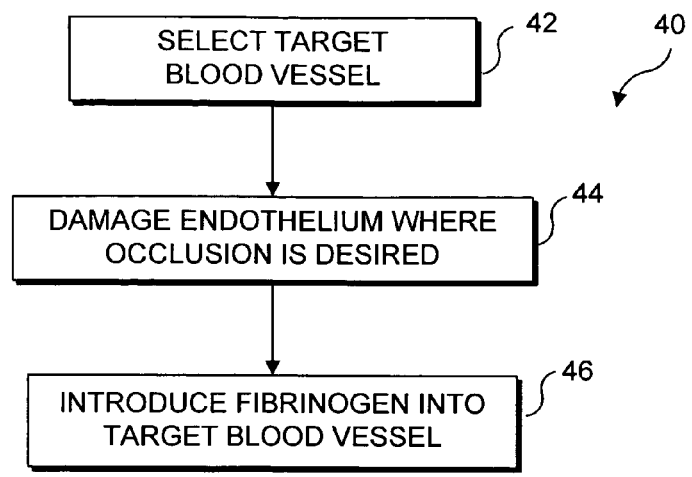
FIG. 4A is a flow chart indicating a sequence of logical steps implemented to selectively occlude a blood vessel in accord with the present invention.

Referring to FIG. 4A, a flowchart 40 illustrates a sequence of steps that can be used to selectively occlude a blood vessel in accord with the present invention. In a block 42 a target blood vessel is selected. In a block 44, endothelial cells are damaged in a portion of the target blood vessel where an occlusion is desired. In a block 46, additional fibrinogen (i.e., fibrinogen at levels over and above that naturally present in the blood vessel) is introduced into the target blood vessel. As discussed above, when endothelial cells are damaged the coagulation cascade results in the formation of a relatively small fibrin clot proximate the damaged endothelial cells. Several factors are involved in the formation of the initial small fibrin clot, including the migration of platelets to the highly thrombogenic tissue exposed by the damaged endothelial cells. Adding additional fibrinogen into the blood vessel results in the enlargement of the original fibrin clot.

Because the clinician can control the location of the damage to the endothelial cells, the clinician can control the location of the occlusion that is formed. This capability enables a clinician to selectively generate an occlusion in a blood vessel at a desired location.

Figure 4B:
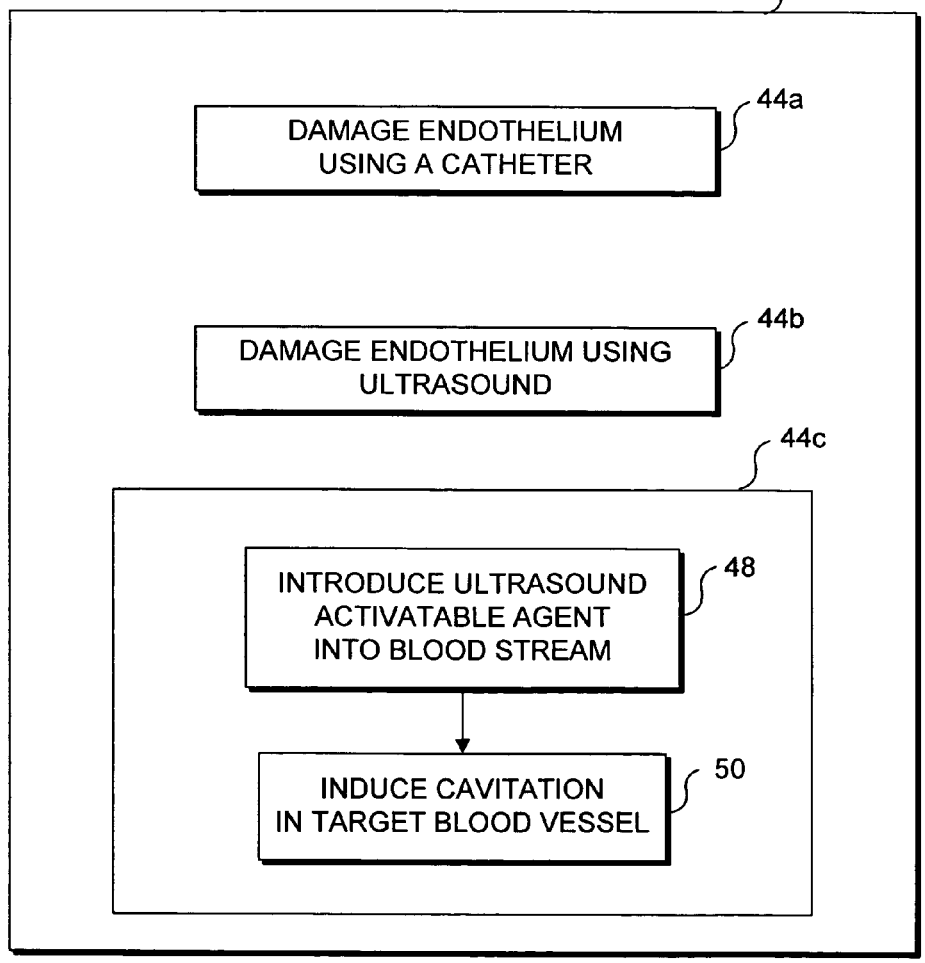
FIG. 4B is a block diagram indicating a plurality of different techniques that can be used to selectively damage endothelial cells in a blood vessel, to initiate the coagulation cascade of FIG. 3.

Several different techniques can be used to damage the endothelial cells lining the blood vessels. FIG. 4B is a block diagram schematically illustrating techniques that can be used to damage endothelial cells. It should be understood that these techniques are exemplary, and while one of these techniques represents a particularly preferred technique, these enumerated techniques are not intended to limit the scope of the present invention. A block 44a indicates that the endothelial cells can be damaged using a catheter. Several different types of catheters can be employed to selectively damage endothelial cells. For example, a balloon catheter 54 can be introduced into a blood vessel 52, with the portion of the catheter corresponding to expandable member/balloon 56 being selectively positioned proximate a portion of the blood vessel where an occlusion is desired, as indicated in FIG. 5A. The balloon is then inflated sufficiently to damage endothelial cells 58 contacted by expandable member/balloon 56. If desired, a portion 62 of expandable member/balloon 56 contacting the vessel walls can be formed of an abrasive or rough material, to ensure that endothelial cells 58 contacted by the expandable member are damaged. It may be desired to move the catheter back and forth slightly (i.e., longitudinally in the blood vessel) while the expandable member is inflated, to abrade the endothelial cells.

FIG. 5B schematically illustrates a catheter 66 advanced into a blood vessel 66 until a distal tip 68 of catheter 66 is disposed proximate to a portion of blood vessel 64 where an occlusion is desired. A tool 70 is used to selectively damage endothelial cells 72. Tool 70 can be implemented in several ways. A guide wire having a sharpened tip can be used for tool 70, the sharpened tip being used to damage the endothelial cells. Tool 70 can be an electrode configured to cauterize endothelial cells, or as a needle configured to inject a toxic material, although such embodiments are likely needlessly complicated, particularly as compared to a tool configured to mechanically damage or abrade the endothelial cells.

Referring once again to FIG. 4B, a block 44b schematically indicates that endothelial cells can be damaged using ultrasound. As noted above, HIFU can be used to induce both thermal and mechanical effects and tissue. FIG. 6A illustrates an exemplary use of HIFU therapy applied to a blood vessel to selectively damage endothelial cells in a blood vessel. As noted above, the HIFU therapy results in the formation of a relatively small thrombus approximate the damaged endothelial cells, and the introduction of additional fibrinogen results in the thrombus being enlarged, thereby occluding the blood vessel. In a HIFU therapy probe 74, an acoustic coupling 80 is attached to a therapy transducer 76 that is mounted to a handle 78. A lead 92 couples the transducer to a power supply (not shown). In FIG. 6A, probe 74 is being used to apply HIFU to a portion of a blood vessel 88, at a location where a clinician as determined an occlusion in the blood vessel should be formed. Blood vessel 88 is disposed in tissue 90 below a dermal layer 82 of a patient (not otherwise shown).

While many different acoustic transducers are suitable for HIFU applications, HIFU transducers often exhibit a generally conical-shaped beam 84, and a substantially smaller, generally elliptical focal region 86. When probe 74 is positioned so that focal region 86 is coincident to the portion of blood vessel 88 where a clinician desires an occlusion to be formed, and therapy transducer 76 is energized, endothelial cells proximate to focal region 86 are damaged by the HIFU beam. The interaction of the HIFU beam with the blood vessel that results in damage to the endothelial cells is discussed in greater detail below.

It should be understood that blood vessel 88 is intended simply as a schematic representation of an exemplary blood vessel and is not intended to represent any particular circulatory structure. It should also be understood that suitably configured HIFU therapy probes for treating circulatory structures could be used inside a patient's body (inserted either via a body cavity or via a transdermal incision) and are not limited to external use. The use of an external HIFU therapy probe or a HIFU therapy probe configured for insertion into a body cavity are preferred to inserting HIFU therapy probes into the body via an incision, because the former two techniques are less invasive than the latter technique.

An important component in any type of ultrasound therapy system is the mechanism for coupling the acoustic energy into the tissue. Good acoustic coupling is necessary to efficiently transfer the ultrasound energy from the transducer to the treatment site. The ideal acoustic coupler is a homogenous medium that has low attenuation and an acoustic impedance similar to that of the tissue being treated. Due to its desirable acoustic transmission characteristics, water or hydrogel have commonly been used as the coupling medium in many therapeutic applications of ultrasound.

Several different types of acoustic couplings are known. Acoustic viscous coupling gels can be smeared over the distal end of the probe and on the patient's skin (or tissue layer in a body cavity) to facilitate acoustic coupling. Water is an excellent acoustic coupling medium, and water filled balloons or bladders are often disposed between an acoustic transducer and the skin layer to facilitate acoustic coupling. While the use of aqueous filled membranes is well known, there are some disadvantages to using aqueous filled membranes for acoustic coupling. These disadvantages include a requirement for degassing the aqueous solution (the presence of gas bubbles will significantly impede transmission of the ultrasound waves), sterilization concerns, and containment issues. Hydrogels are solids having a particularly high water content, and are efficient coupling media for diagnostic ultrasound. Hydrogels are hydrophilic, cross-linked, polymer networks that become swollen by absorption of water. The high water content and favorable mechanical properties of hydrogels have made them attractive for a wide range of biomedical applications, including soft contact lenses, maxillofacial reconstruction, burn dressings, and artificial tendons. Since hydrogels consist mostly of water, they inherently have low attenuation and acoustic impedance similar to tissue. They can be formed into rigid shapes and have relatively low material costs. Unlike the ultrasound transmission gels typically used for diagnostic scans, hydrogels can have consistencies similar to soft rubber, and can be formed into relatively rigid, 3D shapes. In one preferred embodiment of the present invention, acoustic coupling 80 is thus implemented using a hydrogel. It should be understood, however, that acoustic coupling 80 can also be implemented using a viscous ultrasound transmission gel or an aqueous-filled membrane.

Acoustic transducer 76 has a fixed focal length. That is, focal region 86 is separated from acoustic transducer 76 by a fixed distance (absent any interactions with matter that would tend to deflect the acoustic waves responsible for focal region 86). Yet, the present invention is not limited to the use of fixed focal length acoustic transducers. For example, phased arrays of acoustic transducers having variable focal lengths can also be employed. However, a fixed focal length acoustic transducer can be utilized to achieve a robust, relatively simple, and useful HIFU therapy probe. In applications where a fixed focal length acoustic transducer is used for HIFU therapy, acoustic coupling 80 can be employed to control the position of focal region 86 relative to the patient. If a relatively thicker acoustic coupling 80 is employed, focal region 86 will be disposed closer to dermal layer 82, while if a relatively thinner acoustic coupling 80 is employed, the focal region will penetrate further below the dermal layer and deeper into the subcutaneous target. Thus, the thickness of acoustic coupling 80 can be used to control the position of the focal region relative to a patient's tissue contacted by the acoustic coupling. As noted above, hydrogels can be formed into relatively rigid, 3D shapes and are relatively inexpensive. Thus, a plurality of hydrogel couplings of different thicknesses can be provided to enable HIFU therapy probe 74 to deliver HIFU to treatment sites disposed at various distances from dermal (or other tissue) layer 82. This effect is readily apparent in FIG. 6B, in which an acoustic coupling 80a replaces acoustic coupling 80 of FIG. 6A, and focal region 86 now coincides with a blood vessel that is disposed closer to dermal layer 82 as compared to FIG. 6A.

Referring now to the interaction of the HIFU beam with blood vessel 88 of FIG. 6A, it should be understood that HIFU therapy can be used to damage endothelial cells based on thermal effects, mechanical effects, or a combination of thermal effects and mechanical effects. To damage endothelial cells based on thermal effects, acoustic transducer 76 is energized using a power level and duty cycle sufficient to induce tissue necrosis (or damage) throughout focal region 86. While this will certainly damage endothelial cells coinciding with focal region 86, it is likely that at least a portion of focal region 86 will coincide with perivascular tissue. Under some circumstances, such as reducing blood loss in an emergency situation, damage to perivascular tissue may be acceptable. However, there are also certainly other circumstances in which it would be desirable to avoid damage to perivascular tissue. Under such circumstances, HIFU therapy can be provided to damage endothelial cells based primarily on mechanical effects and with reduced or minimal thermal effects, thereby avoiding or limiting damage to perivascular tissue.

As discussed above, mechanical damage to tissue associated with HIFU therapy is primarily based on cavitational effects. As noted above, U.S. Pat. No. 5,827,204 describes a technique for using a multi-frequency ultrasound wave for causing vaporous cavitational bubbles in a small focal region of a medical target. A relatively low frequency signal enables optimal growth of microbubbles proximate the target region, while a relatively high frequency signal enables a very narrow range of focus to be achieved, such that only those bubbles disposed in the narrowly defined focal region of the high-frequency signal will undergo vaporous cavitation. In the context of the present invention, the technique described in U.S. Pat. No. 5,827,204 can be used to form bubbles in a blood vessel, such that only those bubbles coinciding with the precisely defined focal region undergo cavitation. This will result in mechanical damage to the endothelial cells proximate the narrowly defined focal region. A relatively small thrombus will be formed proximate the damaged endothelial cells, and additional fibrinogen introduced into the blood vessel in accord with the present invention will result in expansion of the original relatively small thrombus, thereby occluding the blood vessel. Before such a technique is used in a clinical setting, empirical studies in animal models should be conducted to ensure that the formation of bubbles in a blood vessel do not result in any undesirable side effects.

In a particularly preferred embodiment of the present invention, ultrasound activatable agents will be introduced into the blood vessel before HIFU therapy is applied to selectively damage endothelial cells proximate a region in the blood vessel in which a clinician has determined an occlusion should be formed. FIG. 6B schematically illustrates this technique. As discussed above with respect to FIG. 6A, HIFU therapy probe 74 (comprising acoustic transducer 76, handle 78 and lead 92) is used with acoustic coupling 80a to apply acoustic energy to a portion of a blood vessel 88a, at a location where a clinician has determined an occlusion in the blood vessel should be formed. Blood vessel 88a is similarly disposed in tissue 90a below dermal layer 82 of a patient (not otherwise shown). Significantly, an ultrasound activatable agent 16 is introduced into blood vessel 88a before HIFU therapy is applied. The function of ultrasound activatable agent 16 is to undergo cavitation when activated by a pulse of HIFU, the cavitation causing mechanical damage to the endothelial cells. Only the ultrasound activatable agent disposed in generally elliptical focal region 86 will be activated, so that damage to the endothelial cells will be limited to the portion of the blood vessel coincident with focal region 86. In this manner, a clinician will be able to selectively determine where in a blood vessel an occlusion will be formed, simply by controlling the position of focal region 86 relative to the blood vessel. The ultrasound activatable agent can be introduced directly into the blood vessel, or the ultrasound activatable agent can be introduced systemically into the patient's circulatory system. In general, the ultrasound activatable agent comprises micro-bubbles, such as are commonly employed as ultrasound contrast agents. Empirical studies have utilized commercially available Optison® (Amersham Health, Princeton, N.J.) ultrasound contrast agents as ultrasound activatable agents. This technique achieves a similar effect as described above in conjunction with the use of the technique disclosed in U.S. Pat. No. 5,827,204; however, a less complicated ultrasound therapy system is required (i.e., an ultrasound therapy system capable of achieving the multi frequency ultrasound wave required in the technique disclosed in U.S. Pat. No. 5,827,204 is not necessary when ultrasound activatable agents are utilized). Empirical studies utilizing ultrasound contrast agents as an ultrasound activatable agent have achieved damaged endothelial cells using very short pulses of ultrasound. The benefit of using a short duty cycle to activate the ultrasound contrast agents is that such short duty cycles do not deliver the levels of acoustic energy required to induce tissue damaging thermal effects to tissue coincident with focal region 86, which means that there is no appreciable damage to the perivascular tissue.

Significantly, empirical studies have indicated that mechanical damage to endothelial cells induced by cavitation of an ultrasound contrast agent (i.e., of an ultrasound activatable agent) is concentrated in endothelial cells coincident with focal region 86 that are disposed distally of the acoustic transducer. It is believed that this phenomenon is the result of radiation force exerted by the applied acoustic field on the ultrasound activatable agent disposed in the blood vessel coincident with focal region 86. This radiation force appears to rapidly displace bubbles (i.e., ultrasound activatable agent) in the direction of acoustic propagation, resulting in a greater concentration of bubbles near the distal surface (relative to the transducer) of the blood vessel, as compared to the proximal surface (relative to the transducer) of the blood vessel. Because more of the ultrasound activatable agent is disposed near the distal surface of the blood vessel, endothelial damage caused by the cavitation of the ultrasound activatable agent will be greater on the distal surface of the blood vessel. In the empirical studies noted above, a grid-based method was used to quantitatively measure the extent of endothelial damage produced on the proximal and distal endothelial surfaces of vessels exposed to various ultrasound pressure amplitudes, and such studies indicate endothelial damage due to cavitation of an ultrasound activatable agent is substantially localized to the distal surface (relative to the transducer) of the blood vessel.

FIGS. 7A-7F schematically illustrate the use of HIFU and an ultrasound activatable agent to selectively occlude blood vessels in accord with the present invention. In FIG. 7A, a blood vessel 94 includes intact endothelial cells 12, which isolate highly thrombogenic tissue from the blood flowing in blood vessel 94. Platelets 18 (and other naturally occurring blood components, such as red blood cells, white blood cells, and fibrinogen, none of which are specifically shown) and ultrasound activatable agent 16 are present in blood vessel 94. It should be understood that the ultrasound activatable agent can be introduced systemically, or injected directly into the specific blood vessel in question. Focal region 86 of a HIFU therapy transducer is indicated. An arrow 96 indicates a direction of the radiation pressure, which is exerted by the applied acoustic field when the therapy transducer is energized. Note that this radiation pressure causes the ultrasound activatable agent disposed coincident with focal region 86 to migrate to a portion of the blood vessel disposed distally of the HIFU therapy transducer.

FIG. 7B schematically illustrates blood vessel 94 after a pulse of HIFU energy has been applied (the pulse being generally insufficient to induce any thermal damage to the endothelial cells and adjacent tissue), causing the ultrasound activatable agent coincident with focal region 86 to undergo cavitation, thereby damaging the endothelial cells that are coincident with focal region 86 and which are disposed distally of the HIFU therapy transducer.

FIG. 7C schematically illustrates blood vessel 94 after platelets 18 have been attracted to the damaged endothelial cells and exposed highly thrombogenic tissue. Note that normal blood flow causes additional ultrasound activatable agent to flow into focal region 86; however, no additional cavitation occurs, because the HIFU therapy transducer need only be energized briefly to damage the endothelial cells to initiate the occlusion process. With respect to FIGS. 7A-7F, it should be understood that the HIFU therapy transducer need only be energized during the step schematically represented by FIG. 7A. Empirical studies indicate that exposure times of about one minute are sufficient to induce cavitation.

FIG. 7D schematically illustrates blood vessel 94 after activated platelets 18 (i.e., those platelets attracted to the damaged endothelial cells and exposed to naturally occurring thrombolytic agents) and the exposed highly thrombogenic tissue have initiated the conversion of naturally occurring blood soluble fibrinogen (not specifically shown) to insoluble fibrin to generate a relatively small fibrin clot 98 (i.e., a thrombus). Fibrin clot 98 will not significantly occlude blood flow in blood vessel 94, and it is unlikely that fibrin clot 98 will grow much larger unless additional steps are implemented.

FIG. 7E schematically illustrates blood vessel 94 after additional amounts of fibrinogen 102 have been introduced into the blood vessel. Fibrinogen is a naturally occurring substance that is present in relatively small amounts in the bloodstream. In the present invention, the introduction of excess amounts of fibrinogen into a blood vessel that includes selectively damaged endothelial cells ensures that the relatively small fibrin clot that naturally forms as a result of damaging endothelial cells is significantly enlarged so as to substantially occlude the blood vessel. The additional fibrinogen can be introduced directly into the blood vessel in question, or it can be introduced systemically. While excess levels of fibrinogen are not desirable for extended periods of time, the excess levels of fibrinogen required during treatment are not expected to pose a significant risk. As indicated in FIG. 7E, the additional fibrinogen can be injected using a syringe 100, or introduced into the bloodstream via an intravenous drip.

FIG. 7F schematically illustrates blood vessel 94 after the additional fibrinogen proximate the damaged endothelial cells has been converted from soluble fibrinogen to insoluble fibrin, thereby expanding the original relatively small fibrin clot to substantially occlude the blood vessel. As discussed in detail above, coagulation is a complicated process involving a plurality of different naturally occurring compounds and enzymes, and involving the highly thrombogenic tissue underlying endothelial cells, as well as activated platelets that are attracted to the damaged endothelial cells.

An important feature of the present invention is that it enables the clinician to selectively determine where an occlusion should be generated in a blood vessel. Wherever that location is, endothelial cells proximate to that location will need to be damaged to initiate the clotting process, and the clotting process is then enhanced by introducing additional amounts of fibrinogen into that vessel. Where the clinician selectively damages the endothelial cells using a catheter, the position of the catheter in the blood vessel can be readily identified using several different technologies. Ultrasound imaging can be used to identify the position of the catheter in the blood vessel. Radiopaque markings can be incorporated into a distal tip of the catheter so that the position of the tip relative to a blood vessel can alternatively be determined by other imaging technologies, as is well known to those of ordinary skill.

With respect to the use of HIFU to selectively damaged endothelial cells in a blood vessel, it is important to recognize the potential for HIFU beams to damage non-target tissue, particularly when a HIFU duty cycle is employed that delivers sufficient acoustic energy to induce thermal tissue damage. Thus, one aspect of the present invention is directed to verifying the location of the focal region of the HIFU transducer relative to the blood vessel, to ensure that the focal region of the HIFU transducer is properly positioned to damage the endothelial cells of the blood vessel proximate a location where a clinician has determined that an occlusion should be generated. If the focal region of the HIFU beam cannot be accurately positioned, the clinician will not be able to selectively occlude a blood vessel with a desired precision.

A particularly preferred embodiment of the present invention synchronizes ultrasound imaging with HIFU to achieve ultrasound image guided HIFU damage to endothelial cells of a blood vessel. Alternatively, Magnetic Resonance Imaging (MRI) can be used as an imaging modality; however, ultrasound imaging has the benefit of requiring less sophisticated and less expensive equipment.

Various combinations of HIFU transducers and imaging transducers can be beneficially employed. The HIFU transducer and imaging transducer can be integrated into a single instrument. Or, a separate HIFU therapy probe and ultrasound imaging probe can be employed. Depending on the location of the blood vessel being targeted, either or both the HIFU transducer and imaging transducer can be disposed external of the patient, or in a body cavity of the patient. For embodiments in which the HIFU transducer and imaging ultrasound transducer are implemented using separate probes, a frame mounting the two probes may be employed to maintain a proper spatial orientation of the two probes.

When administering HIFU therapy, it is very desirable to be able to observe a treatment site, to ensure that thermal lesions or cavitational damage induced by the HIFU therapy is being produced at the desired location. Failure to properly aim the HIFU beam may result in undesired tissue necrosis of non-target tissue, or clot formation where not desired. From a practical standpoint, this goal has not proven easy to accomplish when ultrasound is used to visualize the focal point, because the HIFU beam used for therapy completely saturates the signal provided by the imaging transducer. One analogy that might help to make this problem clear relates to the relative intensities of light. Consider the light coming from a star in the evening sky to be equivalent to the low power imaging ultrasound waves that are reflected from a target area toward the imaging transducer, while the light from the sun is equivalent to the HIFU generated by the therapy transducer. When the sun is shining during the day, the light from the stars is completely overwhelmed by the light from the sun, and a person looking into the sky is unable to see any stars, because the bright light from the sun makes the dim light coming from the stars substantially imperceptible. Similarly, the HIFU emitted by the therapy transducer completely overwhelms the ultrasonic waves produced by the imaging transducer, and any ultrasonic image generated is completely saturated with noise caused by the HIFU emitted from the therapeutic transducer.

As noted above, U.S. Pat. No. 6,425,867 describes a technique for synchronizing HIFU) ultrasound waves with ultrasound imaging waves. U.S. Pat. No. 6,425,867 also describes a technique in which the focal region of the HIFU therapy transducer is identified in ultrasound image before HIFU therapy is implemented, to ensure that the focal region is accurately positioned relative to a particular treatment site. This technique involves energizing the HIFU therapy transducer at relatively low power level, sufficient to change the echogenicity of the tissue proximate to a focal region, without delivering enough acoustic energy to that tissue to cause any thermal damage. This technique enables the focal region of the HIFU therapy transducer to be visualized in an ultrasound image. As long as this positioning occurs before the ultrasound activatable agent is introduced into the bloodstream, no cavitation (and no damage at the endothelial cells lining the blood vessel) will occur until desired.

FIG. 8 schematically illustrates an ultrasound imaging probe 106 being used in connection with therapy probe 74. Before any ultrasound activatable agent is introduced into a blood vessel 104, acoustic transducer 76 is energized at a power level insufficient to induce any thermal damage in tissue coincident with focal region 86. The relative positions of therapy probe 74 and imaging probe 106 are manipulated until focal region 86 is visible in an image plane 108 provided by ultrasound imaging probe 106. If necessary, further manipulations of the relative positions of the imaging and therapy probes can be made until focal region 86 coincides with the portion of the blood vessel in which the clinician desires an occlusion to be generated. At that point, the therapy transducer is de-energized. The ultrasound activatable agent is then introduced into the blood vessel (for example using syringe 100), either systemically or by injection directly into the blood vessel where the clot is to be formed. The therapy transducer is then energized, so that any ultrasound activatable agent coinciding with the focal region of the therapy transducer undergoes cavitation and causes damage to the endothelial cells proximate the focal region of the therapy transducer. As noted above, the damage is concentrated in endothelial cells disposed distally of the therapy transducer. Also as noted above, the therapy transducer is energized using a duty cycle that is insufficient to deliver sufficient acoustic energy to induce thermal damage to tissue coincident with or adjacent to the focal region of the therapy transducer.

Empirical Results

Empirical studies have been performed to verify that it is possible to selectively occlude a blood vessel by selectively damaging endothelial cells lining the blood vessel at a target location (the target location corresponding to a portion of the blood vessel in which the clinician desires an occlusion to be formed), and introducing additional fibrinogen into the blood vessel. The studies are described in a doctoral thesis authored by Joo Ha Hwang titled "Ultrasound-mediated Vascular Bioeffects: Applications for Hemostasis and Sclerotherapy" and submitted to the Bioengineering Department of the University of Washington in February 2005, but not yet published.

In particular, the empirical studies discussed therein not only verify the feasibility of selectively occluding a blood vessel by selectively damaging endothelial cells lining a blood vessel and introducing additional fibrinogen to expand a clot that forms as a result of damaging the endothelial cells in an animal model, but also identify specific ultrasound energy levels capable of inducing cavitation in commercially available ultrasound contrast agents without inducing thermal damage.

One animal model studied was the New Zealand white rabbit. An ultrasound transducer was fabricated using an air-backed, 1.375 inch (34.9 mm) diameter APC 880 disk (available from APC International, Ltd., Mackeyville, Pa.) attached to a custom-built aluminum focusing lens with a 5 cm radius of curvature. The driving electronics employed included a waveform generator (Model 33120A, available from Agilent Technologies, Palo Alto, Calif.) and an RF power amplifier (Model AP-400B, available from EIL, Rochester, N.Y.). The transducer was operated at its resonance frequency of 1.17 MHz. The maximum acoustic pressure amplitudes achievable with this system were 27 MPa peak positive and 9 MPa peak negative. The spatial peak, pulse average intensity (ISPPA) was calculated directly from hydrophone measurements.

The empirical studies demonstrated that vascular endothelial surfaces can be damaged by exposing a blood vessel to HIFU in the presence of an ultrasound activatable agent in a rabbit, and that such damage results in the formation of a non-occlusive fibrin thrombus along the luminal surface of the blood vessel. Vascular occlusion in the animal model was achieved by introducing fibrinogen into the blood vessel including the non-occlusive fibrin thrombus. This nidus of fibrin clot, which is anchored to the damaged endothelial surface, enabled propagation and stabilization of the fibrin clot to occlude the targeted segment of a vein in the rabbit model. Further details of the empirical studies can be found below.

One portion of the empirical studies was directed to verifying that the above identified transducer could deliver bursts of HIFU (1.17 MHz, with a 1 Hz pulse repetition frequency, and 5300 W/cm$^{-2}$ ISPPA, and a 5% duty factor) to tissue elevating the temperature of the target tissue to level levels (i.e. levels in excess of 43° C.). This portion of the empirical studies demonstrated that tissue that is elevated to 43° C. for 1 minute is highly unlikely to exhibit any significant thermal injury, and that shorter duty factors result in less temperature rise, with essentially no temperature elevation noted for duty factors of 0.4% or less.

Seven New Zealand white rabbits were used for an empirical study directed toward confirming that selective occlusion of blood vessels in accord with the present invention could be achieved in an animal model. The transducer employed has been described above. The ultrasound activatable agent employed was Optison® (Amersham Health, Princeton, N.J.), a commercially available ultrasound contrast agent. The ultrasound exposure conditions employed are as follows: 1.17 MHz frequency, 9 MPa peak negative pressure, 5000 cycle pulse, 1 Hz PRF, and 0.43% duty factor. The peak positive and negative pressures applied in this study were +27 and −9 MPa respectively, corresponding to a ISPPA of approximately 5300 Watts/claim$^2$. The spatial peak-temporal average intensity ($I_{SPTA}$), for a 0.43% duty factor, was approximately 23 Watts/cm$^2$. Targeted vessels were exposed at two sites located 4 mm apart for 60 seconds each.

The fibrinogen used in the empirical study was obtained from a fibrin sealant (Tisseel VH fibrin sealant, Baxter Healthcare Corp., Westlake Village, Calif.). The fibrinogen was provided as a vapor-heated, freeze-dried powder (375-575 mg) that was dissolved in a solution of aprotinin (a fibrinolysis inhibitor) prior to injection.

In each animal three (3) vessel segments were targeted for treatment, two of those segments corresponding to control treatments. The three types of treatments included: 1) an injection of fibrinogen only (no ultrasound, no ultrasound contrast agent); 2) an injection of the ultrasound contrast agent (0.5 ml of Optison®) followed by ultrasound exposure, without a subsequent fibrinogen injection; and 3) an injection of the ultrasound contrast agent followed by ultrasound exposure, followed by a fibrinogen injection (up to 0.2 cubic of fibrinogen).

Following treatment, the targeted vessels were evaluated for evidence of vascular occlusion using a vascular Doppler ultrasound probe (pdAccess, Escalon Vascular Access, New Berlin, Wis.). The Doppler probe was used to determine if venous blood flow could be identified in the treated segment. This result was reported as the presence or absence of venous flow. In addition, injection of Evan's blue dye upstream to the treated segment was performed as a method of visual angiography. The findings from injection of Evan's blue dye was reported as occlusion (no flow of blue dye through the treated vessel segment) or no occlusion (blue dye visualized flowing through the treated segment).

At the conclusion of the experiment one animal was euthanized and the remaining six animals were recovered and monitored for 14 days following treatment, then euthanized. The vessels segments were then resected, placed in fixative (10% buffered formalin) and prepared for light microscopy to assess the presence of a vascular thrombus. A pathologist with no knowledge of the treatment protocol graded each vessel with respect to the presence of an occlusive thrombus, the presence of a non-occlusive thrombus, or that no thrombus was present. The primary endpoints of the study were based on acute vessel occlusion, and vessel occlusion 14 days after treatment.

The results of the treatment arm and control arms are given in Table 1. Acute vascular occlusion occurred in all 7 vessels treated with ultrasound in the presence of ultrasound contrast agents, followed by an intravascular injection of fibrinogen. Vascular occlusion was demonstrated by the absence of venous flow using Doppler evaluation of the treated segment. Injection of Evan's blue dye confirmed vessel occlusion with redistribution of flow. Vessels that were injected with fibrinogen, but not targeted with ultrasound, did not occlude with the injection of fibrinogen. Furthermore, no acute systemic reactions occurred as a result of fibrinogen injection. Vessels that were targeted with ultrasound after injection of an ultrasound contrast agent, but were not injected with fibrinogen, did not demonstrate any evidence of vessel occlusion. The p-values in comparing the difference in outcomes between the treatment arm and either of the control arms were p=0.0006 each. In Table 1, UCA refers to ultrasound contrast agent. The data are organized based on the outcome of the test (i.e., based on whether a vessel was occluded or not occluded), where the vessel was treated with one of the following: ultrasound and ultrasound contrast agents (US+UCA); ultrasound, ultrasound contrast agents, and fibrinogen (US+UCA+fibrinogen); and, fibrinogen only.

TABLE 1

Observed frequencies of acute vascular occlusion by treatment group.

| Outcome | US + UCA only | US + UCA + Fibrinogen | Fibrinogen only |
|---|---|---|---|
| Occlusion | 0 | 7 | 0 |
| No occlusion | 7 | 0 | 7 |
| Totals | 7 | 7 | 7 |
|  | | p = 0.0006 | p = 0.0006 |

Vascular occlusion 14 days after treatment was determined by examining histology. A pathologist unfamiliar with the treatment protocol reviewed each slide to assess for complete vascular occlusion, partial vascular occlusion, or no vascular occlusion. There was no evidence of vascular occlusion in either control arm (fibrinogen injection without ultrasound exposure and without the injection of ultrasound contrast agents, and ultrasound exposure in the presence of an ultrasound contrast agent without the subsequent injection of fibrinogen). Slides corresponding to the treatment arm (ultrasound exposure in the presence of an ultrasound contrast agent followed by the subsequent injection of fibrinogen) were graded as including four vessels exhibiting a non-occlusive vascular thrombus and two vessels exhibiting no evidence of vascular occlusion. There was a statistically significant difference (p=0.03) in the number of vessels with partial occlusion by residual intravascular thrombus in the treatment arm as compared with either control arm.

There was no evidence of adverse systemic effects (acute or after 14 days) from injection of fibrinogen. There was no evidence of ulceration or tissue damage in the ultrasound treated vessel segments 14 days following treatment. There was also no evidence of infection at the injection sites.

The empirical study demonstrated the ability to selectively occlude a targeted segment of a rabbit vein by initially targeting the vessel segment with pulsed ultrasound in the presence of an ultrasound contrast agent followed by local injection of fibrinogen. The study indicates that ultrasound induced vascular injury alone (i.e. damage to endothelial cells without the subsequent injection of fibrinogen) appears to be insufficient to result in an occlusive thrombus, as the rabbit vessels so treated were not completely occluded. Increasing the local concentration of fibrinogen by injection appears to provide sufficient substrate to yield an occlusive fibrin thrombus. Injection of fibrinogen alone does not lead to vessel occlusion and also does not result in distant thromboemboli, since fibrinogen is not inherently thrombogenic. It appears that initial damage to the endothelial surface provides a sufficient milieu of endothelial damage, platelet aggregation and activation, and local clotting factors such that a local high concentration injection of fibrinogen results in an occlusive fibrin clot.

Survival studies demonstrate that the vessel occlusion is not durable over 14 days. This is not an unexpected result. The biologic response to an occlusive thrombus is to reestablish normal blood flow. In the case of clots primarily consisting of fibrin, the local activation of the fibrinolytic system regulates the extent of intravascular thrombus formation and its degradation. Prior art techniques that have resulted in the successful long-term occlusion of vessels generally involves a greater degrees of injury to the vessel and perivascular tissue, leading to intense inflammation which is known to promote clot stability. The primary mechanism by which inflammation promotes clot stability is thought to be due to interleukin-l release from inflammatory cells resulting in up regulation of plasminogen activator inhibitor synthesis by endothelial cells which results in down regulation of fibrinolytic activity. The histology of ultrasound treated vessels in this empirical study indicates that such an intense inflammatory response does not occur as a result of ultrasound treatment. Therefore, in order to obtain a durable vascular occlusion, an additional agent that elicits an intense local inflammatory response, such as absolute alcohol, will likely be required. Thus, one aspect of the present invention encompasses the additional step of introducing an inflammatory agent (also referred to as a pro-inflammatory agent), such as absolute alcohol, to promote long-term clot stability.

Yet another aspect of the present invention provides for injecting low doses of thrombin (100 U of thrombin is a sub-thrombogenic dose in the absence of existing endothelial damage) into vessels whose endothelial surfaces have been damaged, to achieve a similar occlusion.

It should be noted that while the disclosure provided above has emphasized the step of introducing fibrinogen (or thrombin) into the blood vessel after selectively damaging endothelial cells lining the blood vessel, to enhance the formation of a clot initiated by damaging the endothelial cells, the present invention also encompasses the occlusion of a blood vessel by selectively damaging endothelial cells lining the blood vessel alone, without the additional introduction of fibrinogen or thrombin into the blood vessel. While this technique has not yet been empirically tested, the empirical data discussed above has substantiated that damaging endothelial cells results in the formation of a clot proximate the damaged endothelial cells. Particularly in relatively small blood vessels, selectively damaging endothelial cells is likely to achieve vessel occlusion due to clotting without requiring the injection of fibrinogen or thrombin. Note that in FIGS. 7A-7F, the initial damage to the endothelial cells is limited to one portion of the blood vessel. To achieve vessel occlusion by selectively damaging endothelial cells alone (i.e., without the contemporaneous introduction of fibrinogen or thrombin), it will be desirable to damage endothelial cells about the circumference of the blood vessel, such that multiple clots (each corresponding to a location where endothelial cells have been damaged) combine to occlude the blood vessel. This concept is schematically illustrated in FIGS. 9A-9D.

FIGS. 9A-9D schematically illustrate a cross-section of a blood vessel 200 lined with endothelial cells 202 (for simplicity, individual endothelial cells have not been shown). In FIG. 9A, endothelial cells have been selectively damaged at a location 204. As described above, a clot 206 will form to partially occlude blood vessel 200, as indicated in FIG. 9B. In the techniques described above, fibrinogen or thrombin would be introduced into the blood vessel to enlarge clot 206 to occlude blood vessel 200. To facilitate occlusion of blood vessel 200 without introducing fibrinogen or thrombin (i.e., to achieve occlusion by selectively damaging endothelial cells alone), endothelial cells at additional locations 204 about the circumference of blood vessel 200 can be damaged, as indicated in FIG. 9C. This damage will result in the generation of a plurality of clots 206, which should merge together to occlude blood vessel 200, generally as indicated in FIG. 9D. As indicated above, it is expected that such a technique will be particularly effective in smaller blood vessels, although this technique should not be considered to be limited to only minor blood vessels. The endothelial cells can be selectively damaged generally as described above with respect to FIGS. 5A, 5B, 6A, and 6B. Note that the use of a suitably configured balloon catheter (FIG. 5A) offers the advantage of simultaneously damaging endothelial cells about the circumference of the blood vessel, while the use of HIFU and agents in which cavitation can be induced by HIFU offers the advantage of a non-invasive technique.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for selectively occluding blood flow in a blood vessel, comprising the steps of:
    (a) selecting a target location in the blood vessel, the target location corresponding to a portion of the blood vessel in which an occlusion of blood flow in the blood vessel is desired; and
    (b) selectively damaging endothelial cells proximate to the target location, such that a fibrin clot develops proximate to the damaged endothelial cells, thereby at least partially occluding blood flow in the blood vessel, where the endothelial cells proximate to the target location are damaged using at least one technique selected from a group consisting of:
    (i) introducing an ultrasound contrast agent into the blood vessel proximate to the target location, and using focused ultrasound to deliver acoustical energy to the ultrasound contrast agent at the target location, where an amount of acoustical energy delivered is sufficient to induce cavitation in the ultrasound contrast agent at the target location, but insufficient to thermally damage tissue proximate to the target location, the endothelial cells being damaged by mechanical forces associated with the cavitation thus induced; and
    (ii) mechanically damaging the endothelial cells using a catheter that has been introduced into the blood vessel.

2. The method of claim 1, wherein the fibrin clot is insufficient to provide a desired degree of occlusion, further comprising the step of introducing additional fibrinogen into the blood vessel, such that the additional fibrinogen is converted to a fibrin proximate to the damaged endothelial cells, thereby enlarging the fibrin clot and occluding blood flow in the blood vessel to a greater degree.

3. The method of claim 2, wherein the step of introducing additional fibrinogen into the blood vessel comprises the step of introducing fibrinogen proximate to the target location.

4. The method of claim 2, wherein the step of introducing additional fibrinogen into the blood vessel comprises the step of introducing fibrinogen systemically.

5. The method of claim 1, wherein the fibrin clot is insufficient to provide a desired degree of occlusion, further comprising the step of introducing additional thrombin into the blood vessel, thereby enlarging the fibrin clot and occluding blood flow in the blood vessel to a greater degree.

6. The method of claim 1, wherein the step of selecting a target location comprises the step of using ultrasound imaging to select the target location.

7. The method of claim 1, wherein the step of introducing the ultrasound contrast agent into the blood vessel comprises the step of introducing the ultrasound contrast agent systemically.

8. The method of claim 1, wherein the step of introducing the ultrasound activatable agent into the blood vessel comprises the step of introducing the ultrasound activatable agent proximate to the target location.

9. The method of claim 1, further comprising the step of introducing a pro-inflammatory agent into the blood vessel after the occlusion has been formed, to enhance the long term stability of the occlusion.

10. A method for selectively occluding blood flow in a blood vessel without causing damage to perivascular tissue, comprising the steps of:
   (a) selecting a target location in the blood vessel, the target location corresponding to a portion of the blood vessel in which an occlusion of blood flow in the blood vessel is desired by a practitioner of the method; and
   (b) damaging endothelial cells proximate to the target location, such that a fibrin clot develops proximate to the damaged endothelial cells, thereby at least partially occluding blood flow in the blood vessel, and wherein the damage to the endothelial cells occurs without damaging adjacent perivascular tissue, where the endothelial cells proximate to the target location are damaged using at least one step selected from a group of steps consisting of:
      (i) introducing an ultrasound contrast agent into the blood vessel proximate to the target location, and using focused ultrasound to deliver acoustical energy to the ultrasound contrast agent at the target location, where an amount of acoustical energy delivered is sufficient to induce cavitation in the ultrasound contrast agent at the target location, endothelial cells being damaged by mechanical forces associated with the cavitation thus induced; an
      (ii) damaging the endothelial cells using a catheter that has been introduced into the blood vessel.

11. The method of claim 10, wherein the fibrin clot is insufficient in size to provide a desired degree of occlusion, further comprising the step of introducing additional fibrinogen into the blood vessel, such that the additional fibrinogen is converted to a fibrin proximate to the damaged endothelial cells, thereby enlarging the fibrin clot and occluding blood flow in the blood vessel to a greater degree.

12. The method of claim 11, wherein the step of introducing the additional fibrinogen into the blood vessel comprises the step of introducing the additional fibrinogen proximate to the target location.

13. The method of claim 11, wherein the step of introducing the additional fibrinogen into the blood vessel comprises the step of introducing the additional fibrinogen systemically.

14. The method of claim 10, wherein the step of selecting a target location in the blood vessel comprises the step of selecting a plurality of target locations generally distributed about the circumference of the blood vessel, and wherein the step of damaging endothelial cells proximate to the target location comprises the step of damaging endothelial cells at the plurality of target locations generally distributed about the circumference of the blood vessel, such that the fibrin clot expands inwardly to occlude the blood flow in the blood vessel.

15. The method of claim 10, wherein the fibrin clot is insufficient to provide a desired degree of occlusion, further comprising the step of introducing additional thrombin into the blood vessel, thereby enlarging the fibrin clot and occluding blood flow in the blood vessel to a greater degree.

16. The method of claim 10, wherein the step of introducing the ultrasound contrast agent into the blood vessel comprises the step of introducing the ultrasound contrast agent systemically.

17. The method of claim 10, wherein the step of introducing the ultrasound contrast agent into the blood vessel comprises the step of introducing the ultrasound contrast agent proximate to the target location.

18. The method of claim 10, wherein the step of using focused ultrasound to deliver acoustical energy to the ultrasound contrast agent at the target location comprises the step of using a duty cycle that is sufficiently short in time to avoid thermally damaging adjacent perivascular tissue.

19. The method of claim 10, further comprising the step of introducing an inflammatory agent into the blood vessel, to enhance the long term stability of the occlusion.

20. A method for selectively occluding blood flow in a blood vessel, comprising the steps of:
   (a) selecting a target location in the blood vessel, the target location corresponding to a portion of the blood vessel in which an occlusion of blood flow in the blood vessel is desired;
   (b) introducing a catheter into the blood vessel, the catheter being configured to selectively damage endothelial cells proximate to the target location; and
   (c) using the catheter to selectively damage endothelial cells proximate to the target location, such that a fibrin clot develops proximate to the damaged endothelial cells, thereby at least partially occluding blood flow in the blood vessel.

21. The method of claim 20, wherein the step of using the catheter to selectively damage endothelial cells proximate to the target location comprises the step of damaging the endothelial cells using an inflatable member.

22. The method of claim 20, wherein the step of using the catheter to selectively damage endothelial cells proximate to the target location comprises the step of damaging the endothelial cells using a tool including a sharpened tip.

23. The method of claim 20, wherein the step of using the catheter to selectively damage endothelial cells proximate to the target location comprises the step of cauterizing the endothelial cells.

24. The method of claim 20, wherein the step of using the catheter to selectively damage endothelial cells proximate to the target location comprises the step of injecting a toxic material into the endothelial cells.

25. A method for selectively occluding blood flow in a blood vessel, comprising the steps of:
   (a) selecting a target location in the blood vessel, the target location corresponding to a portion of the blood vessel in which an occlusion of blood flow in the blood vessel is desired; and
   (b) selectively damaging endothelial cells at a plurality of different sites generally distributed about the circumference of the blood vessel proximate to the target location, such that a fibrin clot develops proximate to the damaged endothelial cells, a distribution of the plurality of different sites about the circumference of the blood vessel resulting in an inward expansion of the fibrin clot, where the endothelial cells proximate the plurality of different sites about the circumference of the blood vessel are damaged using at least one technique selected from a group consisting of:

(i) introducing an ultrasound contrast agent into the blood vessel proximate to the target location, and using focused ultrasound to deliver acoustical energy to the ultrasound contrast agent at the target location, where an amount of acoustical energy delivered is sufficient to induce cavitation in the ultrasound contrast agent at the target location, but insufficient to thermally damage tissue proximate to the target location, the endothelial cells being damaged by mechanical forces associated with the cavitation thus induced; and (ii) damaging the endothelial cells using a catheter that has been introduced into the blood vessel.

* * * * *